(12) United States Patent
Ruff et al.

(10) Patent No.: US 10,548,592 B2
(45) Date of Patent: Feb. 4, 2020

(54) SUTURE METHODS AND DEVICES

(75) Inventors: Gregory L. Ruff, Chapel Hill, NC (US); Jeffrey C. Leung, Raleigh, NC (US); Andrew Kaplan, Hillsborough, NC (US); Matthew A. Megaro, Chapel Hill, NC (US); Stanton D. Batchelor, Holly Springs, NC (US)

(73) Assignees: Ethicon, Inc., Somerville, NJ (US); Ethicon, LLC, Guaynabo, PR (US)

( * ) Notice: Subject to any disclaimer, the term of this patent is extended or adjusted under 35 U.S.C. 154(b) by 1012 days.

(21) Appl. No.: 10/908,539

(22) Filed: May 16, 2005

(65) Prior Publication Data

US 2005/0267531 A1 Dec. 1, 2005

Related U.S. Application Data

(60) Provisional application No. 60/521,528, filed on May 14, 2004.

(51) Int. Cl.
*A61B 17/06* (2006.01)
*A61B 17/04* (2006.01)
(Continued)

(52) U.S. Cl.
CPC ........ *A61B 17/06166* (2013.01); *A61B 17/04* (2013.01); *A61B 17/0401* (2013.01);
(Continued)

(58) Field of Classification Search
CPC ................ A61B 17/04; A61B 17/0401; A61B 17/06166; A61B 2017/0412;
(Continued)

(56) References Cited

U.S. PATENT DOCUMENTS 709,392 A 9/1902 Brown
733,723 A 7/1903 Lukens
(Continued)

FOREIGN PATENT DOCUMENTS

BE 1014364 9/2003
CA 2309844 12/1996
(Continued)

OTHER PUBLICATIONS

US 8,663,276 B2, 03/2014, Leung et al. (withdrawn)
(Continued)

*Primary Examiner* — Gregory A Anderson
(74) *Attorney, Agent, or Firm* — Frost Brown Todd LLC

(57) ABSTRACT

A barbed suture including a body with barbs on the periphery, a pointed end, and an anchor at one end to resist movement of the suture in the direction of the pointed end is provided. One or more limbs on the anchor may be provided, which may be arcuate, of varying lengths, and of varying distribution about the periphery of the suture body. Other anchor designs are provided. Methods of placing single-directional and bi-directional barbed sutures to approximate the tissue on each side of a wound and to position and support tissue in the absence of a wound, as in cosmetic surgery, are provided, and may include terminal J-stitches or S-stitches. Methods of placement may be made with sharp, pointed ends, which may be needles, or insertion devices. Sinusoidal patterns of sutures that have amplitudes generally perpendicular to the resultant holding force of the suture are provided.

28 Claims, 19 Drawing Sheets

(51) Int. Cl.
  *A61B 17/064* (2006.01)
  *A61B 17/11* (2006.01)
  *A61B 17/00* (2006.01)

(52) U.S. Cl.
  CPC ............ *A61B 17/064* (2013.01); *A61B 17/11* (2013.01); *A61B 17/06* (2013.01); *A61B 17/1146* (2013.01); *A61B 2017/00761* (2013.01); *A61B 2017/0412* (2013.01); *A61B 2017/0417* (2013.01); *A61B 2017/0462* (2013.01); *A61B 2017/0464* (2013.01); *A61B 2017/06057* (2013.01); *A61B 2017/06171* (2013.01); *A61B 2017/06176* (2013.01)

(58) Field of Classification Search
  CPC .. A61B 2017/0462; A61B 2017/06171; A61B 2017/06176
  USPC ........................................................ 606/228
  See application file for complete search history.

(56) References Cited

U.S. PATENT DOCUMENTS

| | | | |
|---|---|---|---|
| 789,401 | A | 5/1905 | Acheson |
| 816,026 | A | 3/1906 | Meier |
| 879,758 | A | 2/1908 | Foster |
| 1,142,510 | A | 6/1915 | Engle |
| 1,248,825 | A | 12/1917 | Dederer |
| 1,321,011 | A | 11/1919 | Cottes |
| 1,558,037 | A | 10/1925 | Morton |
| 1,728,316 | A | 9/1929 | Von Wachenfeldt |
| 1,886,721 | A | 11/1932 | O'Brien |
| 2,094,578 | A | 10/1937 | Blumenthal et al. |
| 2,201,610 | A | 5/1940 | Dawson, Jr. |
| 2,232,142 | A | 2/1941 | Schumann |
| 2,254,620 | A | 9/1941 | Miller |
| 2,347,956 | A | 5/1944 | Lansing |
| 2,355,907 | A | 8/1944 | Cox |
| 2,421,193 | A | 5/1947 | Gardner |
| 2,452,734 | A | 11/1948 | Costelow |
| 2,472,009 | A | 5/1949 | Gardner |
| 2,480,271 | A | 8/1949 | Sumner |
| 2,572,936 | A | 10/1951 | Kulp et al. |
| 2,591,063 | A | 4/1952 | Goldberg |
| 2,684,070 | A | 7/1954 | Kelsey |
| 2,736,964 | A | 3/1956 | Lieberman |
| 2,779,083 | A | 1/1957 | Eaton |
| 2,814,296 | A | 11/1957 | Everett |
| 2,817,339 | A | 12/1957 | Sullivan |
| 2,830,366 | A | 4/1958 | Chisena |
| 2,866,256 | A | 12/1958 | Matlin |
| 2,910,067 | A | 10/1959 | White |
| 2,928,395 | A | 3/1960 | Forbes et al. |
| 2,988,028 | A | 6/1961 | Alcamo |
| 3,003,155 | A | 10/1961 | Mielzynski |
| 3,066,452 | A | 12/1962 | Bott et al. |
| 3,066,673 | A | 12/1962 | Bott et al. |
| 3,068,869 | A | 12/1962 | Shelden et al. |
| 3,068,870 | A | 12/1962 | Levin |
| 3,082,523 | A | 3/1963 | Modes et al. |
| 3,123,077 | A | 3/1964 | Alcamo |
| 3,166,072 | A | 1/1965 | Sullivan, Jr. |
| 3,187,752 | A | 6/1965 | Glick |
| 3,206,018 | A | 9/1965 | Lewis et al. |
| 3,209,652 | A | 10/1965 | Burgsmueller |
| 3,209,754 | A | 10/1965 | Brown |
| 3,212,187 | A | 10/1965 | Benedict |
| 3,214,810 | A | 11/1965 | Mathison |
| 3,221,746 | A | 12/1965 | Noble |
| 3,234,636 | A | 2/1966 | Brown |
| 3,273,562 | A | 9/1966 | Brown |
| 3,352,191 | A | 11/1967 | Crawford |
| 3,378,010 | A | 4/1968 | Codling et al. |
| 3,385,299 | A | 5/1968 | LeRoy |
| 3,394,704 | A | 7/1968 | Dery |
| 3,494,006 | A | 2/1970 | Brumlik |
| 3,522,637 | A | 8/1970 | Brumlik |
| 3,525,340 | A | 8/1970 | Gilbert |
| 3,527,223 | A | 9/1970 | Shein |
| 3,545,608 | A | 12/1970 | Berger et al. |
| 3,557,795 | A | 1/1971 | Hirsch |
| 3,570,497 | A | 3/1971 | Lemole |
| 3,586,002 | A | 6/1971 | Wood |
| 3,608,095 | A | 9/1971 | Barry |
| 3,608,539 | A | 9/1971 | Miller |
| 3,618,447 | A | 11/1971 | Goins |
| 3,646,615 | A | 3/1972 | Ness |
| 3,683,926 | A | 8/1972 | Suzuki |
| 3,700,433 | A | 10/1972 | Duhl |
| 3,716,058 | A | 2/1973 | Tanner, Jr. |
| 3,720,055 | A | 3/1973 | de Mestral et al. |
| 3,748,701 | A | 7/1973 | De Mestral |
| 3,762,418 | A | 10/1973 | Wasson |
| 3,825,010 | A | 7/1974 | McDonald |
| 3,833,972 | A | 9/1974 | Brumlik |
| 3,845,641 | A | 11/1974 | Waller |
| 3,847,156 | A | 11/1974 | Trumble |
| 3,889,322 | A | 6/1975 | Brumlik |
| 3,918,455 | A | 11/1975 | Coplan |
| 3,922,455 | A | 11/1975 | Brumlik |
| 3,941,164 | A | 3/1976 | Musgrave |
| 3,963,031 | A | 6/1976 | Hunter |
| 3,977,937 | A | 8/1976 | Candor |
| 3,980,177 | A | 9/1976 | McGregor |
| 3,981,051 | A | 9/1976 | Brumlik |
| 3,981,307 | A | 9/1976 | Borysko |
| 3,985,138 | A | 10/1976 | Jarvik |
| 3,990,144 | A | 11/1976 | Schwartz |
| 4,006,747 | A | 2/1977 | Kronenthal |
| 4,008,303 | A | 2/1977 | Glick et al. |
| 4,027,608 | A | 6/1977 | Arbuckle |
| 4,043,344 | A | 8/1977 | Landi |
| 4,052,988 | A | 10/1977 | Doddi et al. |
| D246,911 | S | 1/1978 | Bess, Jr. et al. |
| 4,069,825 | A | 1/1978 | Akiyama |
| 4,073,298 | A | 2/1978 | LeRoy |
| 4,075,962 | A | 2/1978 | Mabry |
| 4,098,210 | A | 7/1978 | Wright |
| 4,137,921 | A | 2/1979 | Okuzumi et al. |
| 4,182,340 | A | 1/1980 | Spencer |
| 4,186,239 | A | 1/1980 | Mize et al. |
| 4,198,734 | A | 4/1980 | Brumlik |
| 4,204,541 | A | 5/1980 | Kapitanov |
| 4,204,542 | A | 5/1980 | Bokros et al. |
| 4,259,959 | A | 4/1981 | Walker |
| 4,278,374 | A | 7/1981 | Wolosianski |
| 4,300,424 | A | 11/1981 | Flinn |
| 4,311,002 | A | 1/1982 | Hoffmann et al. |
| 4,313,448 | A | 2/1982 | Stokes |
| 4,316,469 | A | 2/1982 | Kapitanov |
| 4,317,451 | A | 3/1982 | Cerwin et al. |
| 4,372,293 | A | 2/1983 | Vijil-Rosales |
| 4,428,376 | A | 1/1984 | Mericle |
| 4,430,998 | A | 2/1984 | Harvey et al. |
| 4,434,796 | A | 3/1984 | Karapetian et al. |
| 4,449,298 | A | 5/1984 | Patz |
| 4,454,875 | A | 6/1984 | Pratt et al. |
| 4,467,805 | A | 8/1984 | Fukuda |
| 4,490,326 | A | 12/1984 | Beroff et al. |
| 4,492,075 | A | 1/1985 | Faure |
| 4,493,323 | A | 1/1985 | Albright et al. |
| 4,505,274 | A | 3/1985 | Speelman |
| 4,510,934 | A | 4/1985 | Batra |
| 4,531,522 | A | 7/1985 | Bedi et al. |
| 4,532,926 | A | 8/1985 | O'Holla |
| 4,535,772 | A | 8/1985 | Sheehan |
| 4,548,202 | A | 10/1985 | Duncan |
| 4,553,544 | A | 11/1985 | Nomoto et al. |
| 4,610,250 | A | 9/1986 | Green |
| 4,610,251 | A | 9/1986 | Kumar |
| 4,635,637 | A | 1/1987 | Schreiber |
| 4,637,380 | A | 1/1987 | Orejola |
| 4,653,486 | A | 3/1987 | Coker |
| 4,669,473 | A | 6/1987 | Richards et al. |

(56) References Cited

U.S. PATENT DOCUMENTS

| | | |
|---|---|---|
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows et al. |
| 4,741,330 A | 5/1988 | Hayhurst |
| 4,750,910 A | 6/1988 | Takayanagi et al. |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuck et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,089,012 A | 2/1992 | Prou |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,258,013 A | 11/1993 | Granger |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green et al. |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst et al. |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |

(56) References Cited

U.S. PATENT DOCUMENTS

| | | |
|---|---|---|
| 5,649,939 A | 7/1997 | Reddick |
| 5,653,716 A | 8/1997 | Malo et al. |
| 5,662,654 A | 9/1997 | Thompson |
| 5,662,714 A | 9/1997 | Charvin et al. |
| 5,669,935 A | 9/1997 | Rosenman et al. |
| D386,583 S | 11/1997 | Ferragamo et al. |
| 5,676,675 A | 11/1997 | Grice |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A * | 10/1999 | Fenton et al. ................. 606/232 |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,042,583 A | 3/2000 | Thompson et al. |
| 6,045,571 A | 4/2000 | Hill et al. |
| 5,320,629 B1 | 5/2000 | Noda et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 * | 12/2002 | Bennett ........................ 606/232 |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |

(56) References Cited

U.S. PATENT DOCUMENTS

| | | |
|---|---|---|
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Ledlein et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Shuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,329,271 B2 | 2/2008 | Koyfman et al. |
| 7,371,253 B2 | 5/2008 | Leung et al. |
| 7,381,211 B2 | 6/2008 | Zamierowski |
| 7,513,904 B2 | 4/2009 | Sulamanidze et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,871,425 B2 | 1/2011 | Jones et al. |
| 7,879,072 B2 | 2/2011 | Bonutti et al. |
| 7,913,365 B2 | 3/2011 | Genova et al. |
| 7,919,112 B2 | 4/2011 | Pathak et al. |
| 7,996,967 B2 | 8/2011 | Genova et al. |
| 7,996,968 B2 | 8/2011 | Genova et al. |
| 8,011,072 B2 | 9/2011 | Genova et al. |
| 8,015,678 B2 | 9/2011 | Genova |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,083,770 B2 | 12/2011 | Ruff et al. |
| 8,100,940 B2 | 1/2012 | Leung et al. |
| 8,118,834 B1 | 2/2012 | Goraltchouk et al. |
| 8,216,273 B1 | 7/2012 | Goraltchouk et al. |
| 8,225,673 B2 | 7/2012 | D'Agostino |
| 8,226,684 B2 | 7/2012 | Nawrocki et al. |
| 8,246,652 B2 | 8/2012 | Ruff |
| 8,308,761 B2 | 11/2012 | Brailovski et al. |
| 8,403,947 B2 | 3/2013 | Ochiai |
| 8,460,338 B2 | 6/2013 | Goraltchouk et al. |
| 8,615,856 B1 | 12/2013 | Gelbart |
| 8,641,732 B1 | 2/2014 | Goraltchouk et al. |
| 8,652,170 B2 | 2/2014 | Leung et al. |
| 8,679,158 B2 | 3/2014 | Leung et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0179718 A1 | 12/2002 | Murokh et al. |
| 2002/0198544 A1 | 12/2002 | Uflacker |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency et al. |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0030354 A1 | 2/2004 | Leung et al. |

(56) References Cited

U.S. PATENT DOCUMENTS

| | | |
|---|---|---|
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0060409 A1* | 4/2004 | Leung et al. ............... 83/522.14 |
| 2004/0060410 A1* | 4/2004 | Leung et al. ............... 83/522.14 |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0237736 A1* | 12/2004 | Genova et al. .................. 83/13 |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Ledlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0185494 A1 | 8/2007 | Reese |
| 2007/0208355 A1 | 9/2007 | Ruff |
| 2007/0213770 A1 | 9/2007 | Dreyfuss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0225764 A1 | 9/2007 | Benavitz et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |

(56) References Cited

U.S. PATENT DOCUMENTS

| | | |
|---|---|---|
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0248216 A1 | 10/2008 | Yeung et al. |
| 2008/0255611 A1 | 10/2008 | Hunter |
| 2008/0255612 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Nawrocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0160961 A1 | 6/2010 | Nawrocki et al. |
| 2010/0163056 A1 | 7/2010 | Tschopp et al. |
| 2010/0211097 A1 | 8/2010 | Hadba et al. |
| 2010/0211098 A1 | 8/2010 | Hadba et al. |
| 2010/0230300 A1 | 9/2010 | Hunter et al. |
| 2010/0239635 A1 | 9/2010 | McClain et al. |
| 2010/0292718 A1 | 11/2010 | Sholev et al. |
| 2010/0298637 A1 | 11/2010 | Ruff |
| 2010/0298639 A1 | 11/2010 | Leung et al. |
| 2010/0298848 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298874 A1 | 11/2010 | Leung et al. |
| 2010/0298875 A1 | 11/2010 | Leung et al. |
| 2010/0298876 A1 | 11/2010 | Leung et al. |
| 2010/0298879 A1 | 11/2010 | Leung et al. |
| 2010/0298880 A1 | 11/2010 | Leung et al. |
| 2010/0313729 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0022086 A1 | 1/2011 | D'Agostino et al. |
| 2011/0046668 A1 | 2/2011 | Goraltchouk et al. |
| 2011/0046669 A1 | 2/2011 | Goraltchouk et al. |
| 2011/0093010 A1 | 4/2011 | Genova et al. |
| 2011/0106152 A1 | 5/2011 | Kozlowski |
| 2011/0125188 A1 | 5/2011 | Goraltchouk et al. |
| 2011/0130774 A1 | 6/2011 | Criscuolo et al. |
| 2011/0166597 A1 | 7/2011 | Herrmann et al. |
| 2011/0264138 A1 | 10/2011 | Avelar et al. |
| 2011/0288583 A1 | 11/2011 | Goraltchouk et al. |
| 2011/0319932 A1 | 12/2011 | Avelar et al. |
| 2012/0101522 A1 | 4/2012 | Megaro et al. |
| 2012/0109188 A1 | 5/2012 | Viola |
| 2012/0245659 A1 | 9/2012 | Matthews |
| 2013/0072971 A1 | 3/2013 | Kim et al. |
| 2013/0103078 A1 | 4/2013 | Longo et al. |
| 2013/0165971 A1 | 6/2013 | Leung et al. |
| 2013/0172931 A1 | 7/2013 | Gross et al. |
| 2013/0180966 A1 | 7/2013 | Gross et al. |
| 2013/0204295 A1 | 8/2013 | Hunter et al. |
| 2013/0226233 A1 | 8/2013 | D'Agostino et al. |
| 2013/0226234 A1 | 8/2013 | Avelar et al. |
| 2013/0238021 A1 | 9/2013 | Gross et al. |
| 2013/0238022 A1 | 9/2013 | Gross et al. |
| 2013/0245684 A1 | 9/2013 | Ruff et al. |
| 2013/0317545 A1 | 11/2013 | Gross et al. |
| 2014/0039527 A1 | 2/2014 | Avelar et al. |

FOREIGN PATENT DOCUMENTS

| | | |
|---|---|---|
| CN | 1053553 A | 8/1991 |
| CN | 2640420 | 9/2004 |
| DE | 1810800 | 6/1970 |
| DE | 03227984 | 2/1984 |
| DE | 4302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0428253 B1 | 5/1991 |
| EP | 0513713 | 5/1992 |
| EP | 0632999 | 1/1995 |
| EP | 0513736 | 2/1995 |
| EP | 0464479 | 3/1995 |
| EP | 0464480 | 3/1995 |
| EP | 0576337 B1 | 5/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 1075843 | 2/2001 |
| EP | 0705567 | 3/2002 |
| EP | 0673624 | 8/2002 |
| EP | 0839499 | 9/2003 |
| EP | 0755656 | 12/2003 |
| EP | 1525851 | 4/2005 |
| EP | 1532942 | 5/2005 |
| EP | 0826337 | 12/2005 |
| EP | 0991359 | 11/2007 |
| EP | 2036502 | 3/2009 |
| EP | 1948261 | 11/2010 |
| EP | 1726317 | 7/2012 |
| FR | 2619129 | 2/1989 |
| FR | 2693108 | 6/1992 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 54-116419 | 9/1979 |
| JP | 63-288146 | 11/1988 |
| JP | 001113091 | 5/1989 |
| JP | 3-165751 | 7/1991 |
| JP | 4-096758 | 3/1992 |
| JP | 4-266749 | 9/1992 |
| JP | 9-103477 | 4/1997 |
| JP | 410085225 | 4/1998 |
| JP | 11-313826 | 11/1999 |

(56) References Cited

FOREIGN PATENT DOCUMENTS

| | | |
|---|---|---|
| JP | 11332828 | 12/1999 |
| JP | 2002-059235 | 2/2002 |
| JP | 2003-275217 | 9/2003 |
| JP | 2009-118967 | 6/2009 |
| KR | 10-2005-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 1996/006565 | 3/1966 |
| WO | WO 1986/000020 | 1/1986 |
| WO | WO 1987/001270 | 3/1987 |
| WO | WO 1988/009157 | 12/1988 |
| WO | WO 1989/005618 | 6/1989 |
| WO | WO 1990/009149 | 8/1990 |
| WO | WO 1990/014795 | 12/1990 |
| WO | WO 91/07916 A1 | 6/1991 |
| WO | WO 1992/022336 | 12/1992 |
| WO | WO 1995/016399 | 6/1995 |
| WO | WO 1995/029637 | 11/1995 |
| WO | WO 98/52473 | 11/1998 |
| WO | WO 1998/055031 | 12/1998 |
| WO | WO 99/21488 | 5/1999 |
| WO | WO 1999/033401 | 7/1999 |
| WO | WO 1999/052478 | 10/1999 |
| WO | WO9959477 A1 | 11/1999 |
| WO | WO 1999/062431 | 12/1999 |
| WO | WO 00/51658 | 9/2000 |
| WO | WO 2000/051685 | 9/2000 |
| WO | WO 2001/006952 | 2/2001 |
| WO | WO 2001/056626 | 8/2001 |
| WO | WO 2003/001979 | 1/2003 |
| WO | WO 2003/003925 | 1/2003 |
| WO | WO 2003/017850 A2 | 3/2003 |
| WO | WO 03/045255 | 6/2003 |
| WO | WO 2003/077772 | 9/2003 |
| WO | WO 2003/092758 | 11/2003 |
| WO | WO 03/103972 A1 | 12/2003 |
| WO | WO 2003/103733 | 12/2003 |
| WO | WO 2003/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/128113 | 10/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/052007 | 5/2010 |
| WO | WO 2011/053375 | 5/2011 |
| WO | WO 2011/090628 | 7/2011 |
| WO | WO 2011/139916 | 11/2011 |
| WO | WO 2011/140283 | 11/2011 |

OTHER PUBLICATIONS

McKenzie, A.R.; "An Experimental Multiple Barbed Suture for the Long Flexor Tendons of the Palm and Fingers", The Journal of Bone and Joint Surgery, vol. 49B, No. 3, Aug. 1967, pp. 440-447.

"Drilled End Surgical Needles", B.G. Sulzle, Inc., Syracuse, New York, Jul. 2002.

Sulamanidze, M.A., et al.; "Facial Lifting with "Aptos" Threads", Jul. 18, 2001, www.fonendo.com, pp. 1-6.

Dattilo, Jr., Philip P., et al.; "Medical Textiles: Application of an Absorbable Barbed Bi-directional Surgical Suture", Journal of Textile and Apparel, Technology and Management, vol. 2, Issue 2, Spring 2002; RTP, North Carolina.

"Up Lifting (Aptos Threads)" http://www.ccpr.com.br/upl-l.htm, Aug. 19, 2002, pp. 1-2.

Han, Hougtao, et al.; "Mating and Piercing Micromechanical Structures for Surface Bonding Applications" Micro Electro Mechanical Systems, (MEMS-91), Nara, Japan, Jan. 31-Feb. 2, 1991. CH2957-9/91. pp. 253-258. 1991.

Buncke, Jr., H. J., et al.; "The Suture Repair of One-Millimeter Vessels" Micro-Vascular Surgery; Report of First Conference, Oct. 6-7, 1966. pp. 24-35 (esp. p. 34), 1966; USA.

Sulamanidze, M.A., et al.; "Removal of Facial Soft Tissue Ptosis With Special Threads" Dermatol Surg 2002, 28, pp. 367-371; Blackwell Publishing, Inc.

Declaration of Dr. Gregory L. Ruff, Dated Aug. 19, 2005, 8 pages, with Exhibits A-E.

Sulamanidze, M.D., M.A.; Shiffman, M.D., J.D., M.A.; Paikidze, M.D., T.G.; Sulamanidze, M.D., G.M.; Gavasheli, M.D., L.G., "Facial Lifting with APTOS Threads," International Journal of Cosmetic Surgery and Anesthetic Dermatology, No. 4, (2001), pp. 1-8.

Bacci, Pier Antonio, "Chirurgia Estetica Mini Invasiva Con Fili Di Sostegno", Collana di Arti, Pensiero e Scienza; Minelli Editore—2006; 54 pgs.

Behl, Marc et al., "Shape-Memory Polymers", Materials Today Apr. 2007; 10(4); 20-28.

Belkas, J. S. et al., "Peripheral nerve regeneration through a synthetic hydrogel nerve tube", Restorative Neurology and Neuroscience 23 (2005) 19-29.

Bellin, I. et al., "Polymeric triple-shape materials", Proceedings of the National Academy of Sciences of the United States of America Nov. 28, 2006; 2103(48):18043-18047.

Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.

Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.

Bunnell, S. 'Gig pull-out suture for tendons' J Bone Joint Surg. Am (1954) vol. 36A, No. 4 pp. 850-851.

CCPR Centro De Cirurgia Plastica e Reabilitacao 'Up Lifting (Aptos Threads) http:/ /ccpr.com.br/up1-1.htm, Aug. 19, 2002 pp. 1-2.

Dahlin, Lars, "Techniques of Peripheral Nerve Repair", Scandinavian Journal of Surgery 97: 310-316, 2008.

Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.

(56) References Cited

OTHER PUBLICATIONS

Datillo, Jr., P. et al 'Tissue holding performance of knotless absorbable sutures' Society for Biomaterials 29th Annual Meeting Transactions (2003) p. 101.
De Persia, Raül et al., "Mechanics of Biomaterials: Sutures After the Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg. J. Mar. 26, 2006(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006(2): 2 pages.
Gross, R.A. et al 'Biodegradable Polymers for the Environment' Science (2002) vol. 297, Issue 5582 pp. 803.
Ingle, N.P. et al 'Barbed Suture Anchoring Strength: Applicability to Dissimilar Polymeric Materials' College of Textiles, North Carolina State University, 7th World Biomaterials Congress 2004, 1 page.
Ingle, N.P. et al 'Mechanical Performance and Finite Element Analysis of Bi-directional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.
Jennings et al 'A New Technique in primary tendon repair' Surg. Gynecol. Obstet. (1952) vol. 95, No. 5 pp. 597-600.
Jeong, H.E. et al 'A nontransferring dry adhesive with hierarchial polymer nanohairs' PNAS 106 (14) pp. 5639-5644 (2009).
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[(ϵ-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al 'Biodegradable, Elastic Shape-Memory Polymers for Potential Biomedical Applications' (2002) Science vol. 296 pp. 1673-1676.
Lendlein, A. et al 'Shape-Memory Polymers' Agnew Chem. Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al 'Performance Enhancement of a Knotless Suture via Barb Geometry Modifications' 7th World Biomaterials Congress 2004, 1 page.
Li, Y.Y. et al 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Madhave et al 'A biodegradable and biocompatible gecko-inspired tissue adhesive' PNAS 105(7) pp. 2307-2312 (2008).
Maitland et al., "Prototype laser-activated shape memory polymer foam device for embolic treatment of aneurysms", Journal of Biomedical Optics May/Jun. 2007;12(3): pp. 030504-1 to 030504-3.
Malina, M. et al 'Endovascular AAA Exclusion: Will Stents with Hooks and Barbs Prevent Stent-Graft Migration' Journal Endovascular Surgery (1998) vol. 5 pp. 310-317.
Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Martin, D.P. et al 'Medical applications of poly-4-hydroxybutyrate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
Middleton and Tipton 'Synthetic Biodegradable Polymers as Medical Devices' (1998) Medical Plastics and Biomaterials Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http:/ /www.physorg.com/news117214996.html>.
Murtha et al., "Evaluation of a Novel Technique for Wound Closure Using a Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures a Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures a Novel Approach to Soft Tissue Approximation", Canada, Angiotech Pharmaceuticals, Inc., Second Edition Aug. 2008: 20 pages.
Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, 8 2007-2009: 27 pages.
Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, 8 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.

(56) References Cited

OTHER PUBLICATIONS

Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects—Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen (1987) pp. 417-426.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, MD, M.A., et al., "Soft tissue lifting in the mid-face: old philosophy, new approach-internal stitching technique (APTOS Needle)", Plastic and Aesthetic Surgery Clinic Total Sharm, Moscow, Russia, (2005):15-29.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Communication of a Notice of Opposition re: EP05750101.7 dated Jul. 8, 2014.
Communication from EPO re: 10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015905.8 dated Oct. 2, 2007, 2 pages.
European Search Report for EP07015906 dated Oct. 2, 2007.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011868.6 dated Dec. 6, 2010, 2 pages.
European Search Report for EP10011869 dated Jan. 20, 2011.
European Search Report for EP10011871.0 dated Dec. 3, 2010, 2 pages.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report on Patentability re: PCT/US2008/064921 dated Dec. 1, 2009.
International Preliminary Report on Patentability re: PCT/US2008/0075849 dated Mar. 16, 2010.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/034703 dated Aug. 24, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2009/044274 dated Nov. 17, 2010.
International Preliminary Report re: PCT/US2011/035431 dated Nov. 6, 2012.
International Preliminary Report on Patentability re: PCT/US2011/040014 dated Dec. 14, 2012.
International Preliminary Report re: PCT/US2011/059238 dated May 7, 2013.
International Search Report for PCT/US1994/09631 dated Dec. 9, 1994.
International Search Report for PCT/US1998/10478 dated Sep. 23, 1998.
International Search Report for PCT/US2002/20449 dated May 20, 2003.
International Search Report for PCT/US2002/027525 dated Dec. 9, 2002, 3 pages.
International Search Report for PCT/US2003/030424 dated Nov. 1, 2004.
International Search Report for PCT/US2003/030664 dated May 25, 2004.
International Search Report for PCT/2003/030666 dated Dec. 15, 2004.
International Search Report for PCT/US2003/025088 dated Dec. 29, 2003.
International Search Report re: PCT/US2003/030674 dated Sep. 2, 2004.
International Search Report re: PCT/US2004/014962 dated Feb. 24, 2005.

(56) References Cited

OTHER PUBLICATIONS

International Search Report for PCT/US2005/017028 dated Mar. 26, 2008.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report for PCT/US2011/059238 dated May 21, 2012.
International Search Report for PCT/US2012/030441 dated Sep. 27, 2012.
International Search Report for PCT/US2012/041001 dated Sep. 26, 2012.
Partial European Search Report re: EP05025816 dated Mar. 20, 2006.
Partial European Search Report re: EP13168122 dated Feb. 21, 2014.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Singapore Search Report for Singapore Patent Application No. 201103117-6 dated Mar. 8, 2013.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 05750101 dated Apr. 7, 2010.
Supplementary European Search Report re: 07017663 dated Nov. 7, 2007.
Croce, MD, E., et al., "Intracorporeal Knot-Tying and Suturing Techniques in Laparoscopic Surgery: Technical Details," JSLS, 2000, 4:17-22, 6 pgs.
Australian Office Action, Patent Examination Report No. 1, dated Sep. 19, 2013 for Application No. AU 2012201433, 5 pgs.
Australian Office Action, Patent Examination Report No. 2, dated Oct. 14, 2014 for Application No. AU 2012201433, 8 pgs.
European Search Report and Written Opinion dated Jan. 25, 2018 for Application No. EP 17178134.7, 9 pgs.
European Examination Report dated May 6, 2011 for Application No. EP 05750101.7, 5 pgs.
European Decision Rejecting Opposition and Minutes of Oral Proceedings held Nov. 16, 2015 for Application No. EP 05750101.7 and Patent No. EP 1761176, Dec. 10, 2015, 18 pgs.
European Notice of Appeal of Opposition Decision filed Feb. 17, 2016 for Application No. EP 05750101.7 and Patent No. EP 1761176, 4 pgs.
European Statement of Grounds of Appeal and Declaration of Tim Kosa dated Apr. 26, 2016 for Application No. EP 05750101.7 and Patent No. EP 1761176, 22 pgs.
European Reply to Notice of Appeal dated Sep. 6, 2016 for Application No. EP 05750101.7 and Patent No. EP 1761176, 18 pgs.
European Search Report and Written Opinion dated Mar. 20, 2014 for Application No. EP 13168117.3, 9 pgs.
European Examination Report dated Mar. 17, 2016 for Application No. EP 13168117.3, 3 pgs.
European Examination Report dated Mar. 11, 2016 for Application No. EP 13168122.3, 4 pgs.
International Preliminary Report on Patentability dated Feb. 10, 2009 for Application No. PCT/US2005/017028, 4 pgs.
Japanese Office Action, Notification of Reasons for Regusal, dated Oct. 4, 2010 for Application No. JP 2007-513452, 6 pgs.
Japanese Office Action, Decision of Refusal, dated Jun. 7, 2011 for Application No. JP 2007-513452, 4 pgs.
Japanese Office Action, Report of Reconsideration by Examiner before Appeal, dated Nov. 15, 2011 for Application No. JP 2007-513452, 4 pgs.
Japanese Office Action, Notification of Reasons for Refusal, dated Apr. 9, 2013 for Application No. JP 2011-223686, 6 pgs.
Japanese Office Action, Decision of Refusal, dated Nov. 20, 2013 for Application No. JP 2011-223686, 4 pgs.
Japanese Office Action, Report of Reconsideration by Examiner before Appeal, dated May 7, 2014 for Application No. JP 2011-223686, 4 pgs.
Korean Office Action, Written Opinion to the Notification of Reason for Refusal, dated Jan. 20, 2012 for Application No. KR 10-2006-7023828, 9 pgs.
Australian Office Action, Examiner's First Report on Patent Application No. 2005244886, dated Mar. 30, 2010, 2 pages.
Australian Office Action, Examiner's Report No. 2 on Patent Application No. 2005244886, dated Sep. 30, 2011, 4 pgs.
Canadian Office Action dated Jul. 4, 2012 for Application No. CA 2,566,438, 2 pgs.
Chinese Office Action, First Office Action and Search Report, dated Feb. 1, 2016 for Application No. CN 201410562195.9, 5 pgs.
Chinese Office Action, Decision on Rejection, dated Dec. 1, 2010 for Application No. CN 200580023753.3, 12 pgs.
Chinese Office Action, Third Office Action, dated May 24, 2012 for Application No. CN 200580023753.3, 3 pgs.
Indian Office Action, First Examination Report, dated Sep. 25, 2013 for Application No. 6741/DELNP/2006, 2 pgs.
Japanese Office Action, Notification of Reasons for Refusal, dated Mar. 12, 2013 for Application No. 2007-513452, Trial against Examiner's Decision of Refusal No. 2011-21887, 3 pgs.
Singaporean Office Action, Search and Examination Report, dated Apr. 19, 2010 for Application No. SG 200607803-4, 6 pgs.

* cited by examiner

SUTURE METHODS AND DEVICES

CROSS REFERENCE

This application claims priority from co-pending U.S. provisional application 60/521,528, filed May 14, 2004, by the inventors hereof, the entire disclosure of which is incorporated herein by reference.

BACKGROUND

The present invention relates generally to methods and devices for joining or positioning bodily tissue in surgical applications and wound repair, and more particularly to a surgical suturing method and devices for joining or positioning bodily tissue using a suture having a plurality of barbs that permit the suture to be pulled through the tissue in one direction but resist movement of the suture relative to the tissue in the opposite direction.

Single-directional barbed sutures have a plurality of barbs that permit the suture to be pulled through tissue in one direction, but resist movement of the suture in the tissue in the opposite direction. Such sutures may have one end that is pointed to allow penetration and passage through tissue in the one direction and another end that is an anchor which engages the tissue at the initial insertion point to prevent further movement in the one direction. Bi-directional barbed sutures may have barbs extending in one direction at one end and opposing barbs at the other end, preventing movement of the suture through tissue in either direction between two pointed ends.

Methods for placement of barbed sutures in tissue include, but are not limited to, straight, zig-zag, and curvilinear patterns such as alpha, sinusoidal, and corkscrew. In general such patterns terminate in an alignment coincident with the pattern, meaning, for example, that a straight pattern terminates along a straight path, a sinusoidal pattern terminates along a sinusoidal path, and so forth.

Barbed sutures may be used to approximate tissue adjacent to a wound or a tissue separation, or to position and support tissue where there is no wound in procedures such as cosmetic surgery.

SUMMARY

According to the present invention a barbed suture is provided including an elongated body with a cross section, where the cross section has a transverse length, one pointed end, a plurality of cuts in the elongated body providing a plurality of barbs extending from the periphery of the body and tapering from a broad base to a narrow tip. The barbs yield toward the suture body during movement of the suture through the tissue in the direction of movement of the pointed end and the barbs resist movement of the suture through the tissue in a direction opposite the direction of movement of the pointed end. The anchor includes a loop at one end. The elongated body may pass through the loop end to secure tissue as an anchor, the anchor preventing movement of the suture in the direction of movement of the pointed end. In one embodiment a needle is present at the pointed end. In various embodiments; the barbed suture comprises a plurality of barbs characterized by a barb cut depth (Dc), and/or a barb cut angle (Ø), and/or a barb cut length (Lc), and/or a longitudinal distance between barbs cut into the elongated body. For example, the ratio of the barb cut depth to the transverse length may be about 0.05 to about 0.6; the barb cut angle may range from 140 to 175 degrees; the ratio of the barb cut length to transverse length may be about 0.2 to about 2; and/or the ratio of the longitudinal distance between barbs to the transverse length may be about 0.1 to 6. In various embodiments, the looped anchor may be collapsible, may be formed of a bio-absorbable material, may be formed of a non-absorbable material which may optionally be a polymer. In one embodiment the elongated body is generally circular in cross-section, while in another embodiment the elongated body has a non-circular cross sectional shape. The elongated body may be flexible and substantially nonresilient. The barbs may be arranged in a helical pattern, e.g., where the number of barbs in a helical pattern that occupy one revolution is not an integer. The barbs may be arranged in three rows along the elongated body, where the rows are spaced 120 degrees from one another around the circumference of the elongated body. The transverse length of the elongated body may be about 100 to 500 microns. The barbs may be staggered along the elongated body.

Also according to the present invention is a method of placing a barbed suture in bodily tissue. The suture includes at least one pointed end and a central portion having barbs that allow movement of the suture in the direction of movement of the pointed end and resist movement of the suture away from the direction of movement of the pointed end. The method includes inserting the pointed end of the suture in the tissue, and then advancing the suture through the tissue such that the central portion is disposed along a first path. The suture deviates from the first path proximate to the at least one pointed end of the suture along a second path, and the second path forms an angle with the projected first path, had the suture remained on the first path, of at least approximately 30 degrees.

Further according to the present invention, a method of placing a barbed suture in bodily tissue to approximate tissue on each side of a wound is provided. The suture includes at least one pointed end and a central portion having barbs that allow movement of the suture in the direction of movement of the pointed end and resist movement of the suture away from the direction of movement of the pointed end. The method includes inserting the pointed end of the suture in the tissue and then advancing the suture through the tissue along a first path. Then the suture deviates from the first path to follow a second path generally disposed laterally away from the wound. The suture further deviates from the second path proximate to the at least one pointed end of the suture along a third path, and the third path forms an angle with the projected second path, had the suture remained on the second path, of at least approximately 30 degrees.

Yet further in accordance with the present invention, a method of placing a single-directional barbed suture in bodily tissue to approximate a wound is provided. The suture includes an elongated body, one pointed end, one end terminating in an anchor, and a plurality of barbs extending from the periphery of the body. The anchor extends outside the periphery of the body to a greater degree than the barbs. The barbs permit movement of the suture through the tissue in the direction of movement of the pointed end and prevent movement of the suture in a direction opposite the direction of movement of the pointed end. The anchor prevents movement of the suture in the direction of movement of the pointed end. The method includes inserting the pointed end of the suture into one face of the wound and advancing the suture through the tissue until the anchor achieves adequate holding strength in the tissue to resist further movement in the tissue, leaving the anchor embedded in the tissue.

Also in accordance with the present invention, a method of placing a single-directional suture in tissue using an insertion device is provided. The suture includes an elongated body, one pointed end, one end terminating in an anchor, and a plurality of barbs extending from the periphery of the body. The anchor, when extended, extends outside the periphery of the body to a greater degree than the barbs. The barbs permit movement of the suture through the tissue in the direction of movement of the pointed end and prevent movement of the suture in a direction opposite the direction of movement of the pointed end. The anchor prevents movement of the suture in the direction of movement of the pointed end. The insertion device includes a tubular element in which the suture body is at least in part initially disposed and having leading and trailing ends with openings therein with the pointed end of the suture proximate to the leading end. The method includes inserting the pointed end of the suture and the leading end of the insertion device into the tissue at an insertion point. The pointed end of the suture and the leading end of the insertion device are pushed through the tissue until reaching an endpoint. The insertion device is gripped and pulled at the trailing end to remove the insertion device. Tissue is manually grouped and advanced along the suture as desired.

Also according to the present invention another method of placing a single-directional suture in tissue using an insertion device is provided. The suture includes an elongated body, one pointed end, one end terminating in an anchor, and a plurality of barbs extending from the periphery of the body. The anchor, when extended, extends outside the periphery of the body to a greater degree than the barbs. The barbs permit movement of the suture through the tissue in the direction of movement of the pointed end and prevent movement of the suture in a direction opposite the direction of movement of the pointed end. The anchor prevents movement of the suture in the direction of movement of the pointed end. The insertion device includes a tubular element having leading and trailing ends. The method includes inserting the leading end of the insertion device at an insertion point and through the tissue until reaching an endpoint and inserting a leading end of the suture into the insertion device at least until the trailing end of the suture is within the insertion device. A plunger is inserted into the trailing end of the insertion device to abut the trailing end of the suture. The plunger is depressed to push the leading end of the suture out of the insertion device. The insertion device is gripped and pulled at the trailing end to remove the insertion device, leaving the suture in place. The tissue is manually grouped and advanced along the body of the suture as desired.

Also in accordance with the present invention, a method of performing a surgical procedure using a bi-directional barbed suture is provided. The barbed suture includes an elongated body, first and second sharp pointed distal ends for penetrating tissue, and a plurality of barbs extending from the periphery of the body. The barbs on a first portion of the body between the first end of the suture and a first axial location on the body permit movement of the suture through the tissue in a direction of movement of the first end and prevent movement of the suture relative to the tissue in a direction opposite the direction of movement of the first end. The barbs on a second portion of the body between the second end of the suture and a second axial location on the body which is less than the distance from the second end to the first axial location permit movement of the suture through the tissue in a direction of movement of the second end and prevent movement of the suture relative to the tissue in a direction opposite the direction of movement of the second end. An insertion device is used and includes a tubular element and leading and trailing ends. The method includes inserting the leading end of the insertion device at an insertion point in the tissue, and then advancing the leading end of the insertion device through tissue until reaching a selected point. The first pointed end of the suture is inserted into the insertion device at least until one barb extends out of the insertion device. The insertion device is gripped and pulled at the trailing end to remove the insertion device, leaving the full length of the suture in place in the tissue. Tissue is manually grouped and advanced along the body of the suture as desired.

Also in accordance with the present invention is another method of performing a surgical procedure using a bi-directional barbed suture. The barbed suture includes an elongated body, first and second sharp pointed distal ends for penetrating tissue, and a plurality of barbs extending from the periphery of the body. The barbs on a first portion of the body between the first end of the suture and a first axial location on the body permit movement of the suture through the tissue in a direction of movement of the first end and prevent movement of the suture relative to the tissue in a direction opposite the direction of movement of the first end. The barbs on a second portion of the body between the second end of the suture and a second axial location on the body which is less than the distance from the second end to the first axial location permit movement of the suture through the tissue in a direction of movement of the second end and prevent movement of the suture relative to the tissue in a direction opposite the direction of movement of the second end. The method includes inserting the first end of the suture into tissue at an insertion point and then advancing the suture in a generally curvilinear path until the second axial location is at the point of insertion of the first end of the suture and the first end of the suture exits the tissue at an exit point, leaving a length of the first portion of the suture in the tissue. The second end of the suture is inserted into tissue at the insertion point of the first end of the suture. The suture is advanced in a generally curvilinear path distally from the first portion of the suture, until the second end of the suture exits the tissue at an exit point, leaving a length of the second portion of the suture in the tissue. The tissue is manually grouped along the body of the suture as desired. The amplitude of each curvilinear path is generally perpendicular to the resultant holding force exerted by the suture on the tissue.

Also according to the present invention, a method of placing a first single-directional barbed suture and a second single-directional barbed suture in bodily tissue is provided. The sutures each include an elongated body, one pointed end, and one trailing end, and a plurality of barbs extending from the periphery of the body. The barbs permit movement of the suture through the tissue in the direction of movement of the pointed end and prevent movement of the suture in a direction opposite the direction of movement of the pointed end. The method includes inserting the first end of the first suture into tissue at an insertion point and then advancing the suture in a generally curvilinear path until the pointed end of the first suture exits the tissue at an exit point, leaving a length of the body of the first suture in the tissue. The pointed end of the second suture is inserted into tissue at the insertion point of the first suture, and the second suture is advanced in a generally curvilinear path until the pointed end of the second suture exits the tissue at an exit point, leaving a length of the body of the second suture in the tissue. The first and second sutures are tied together at the insertion point. Tissue is manually grouped and advanced along the body of each suture as desired. The amplitude of each curvilinear path is generally perpendicular to the resultant holding force exerted by each suture on the tissue.

Further according to the present invention, another method of placing a single-directional barbed suture in bodily tissue is provided. The suture includes an elongated body, one pointed end, one end terminating in an anchor, and a plurality of barbs extending from the periphery of the body. The anchor extends outside the periphery of the body to a greater degree than the barbs. The barbs permit movement of the suture through the tissue in the direction of movement of the pointed end and prevent movement of the suture in a direction opposite the direction of movement of the pointed end, while the anchor prevents movement of the suture in the direction of movement of the pointed end. The method includes making an incision in the tissue to define a face of the tissue, and inserting the pointed end of the suture in the face of the tissue. The pointed end of the suture is advanced through the tissue to an exit point. The anchor is placed in the incision. The pointed end of the suture is advanced through the tissue until the anchor achieves adequate holding strength in the tissue to resist further movement in the tissue, leaving the anchor embedded in the tissue.

Yet further according to the present invention, a method for joining two ends of severed internal tissue to allow tissue healing and regrowth together of the two ends of the internal tissue in vivo using a single-directional barbed suture is provided. The suture includes an elongated body, one pointed end, one end terminating in an anchor, and a plurality of barbs extending from the periphery of the body. The anchor extends outside the periphery of the body to a greater degree than the barbs. The barbs permit movement of the suture through the tissue in the direction of movement of the pointed end and prevent movement of the suture in a direction opposite the direction of movement of the pointed end, while the anchor prevents movement of the suture in the direction of movement of the pointed end. The method includes inserting the pointed end of the suture into a first end of the internal tissue and pushing the pointed end through the internal tissue along a curvilinear path, proceeding away from the first end and farther into the tissue. The pointed end of the suture is gripped and pulled out of the internal tissue to draw the anchor proximate to the first end of the tissue. The pointed end of the suture is pushed along the periphery of the internal tissue adjacent the exit point. The pointed end is pushed along the curvilinear path and then returns along the path to the first end, and exiting from the first end of the tissue. The pointed end is inserted into an opposing, second end of tissue, and is pushed along a curvilinear path, proceeding away from the second end and farther into the tissue, then returning to the second end, and exiting from the second end of the tissue. The pointed end is inserted into the first end of tissue, pushing the pointed end along a curvilinear path, proceeding away from the second end and farther into the tissue, then returning toward the first end and exiting the tissue.

BRIEF DESCRIPTION OF THE DRAWINGS

For a more complete understanding of the present invention, reference should now be had to the embodiments shown in the accompanying drawings and described below. In the drawings.

DESCRIPTION

As used herein, the term "wound" means a surgical incision, cut, laceration, severed tissue or accidental wound in human skin or other bodily tissue, or other condition where suturing, stapling, or the use of another tissue connecting device might be required.

As used herein, the term "tissue" includes tissues such as skin, bone, muscle, organs, and other soft tissue such as tendons, ligaments and muscle.

Certain other terminology is used herein for convenience only and is not to be taken as a limitation on the invention. For example, words such as "upper," "lower," "left," "right," "horizontal," "vertical," "inward," "outward," "upward," and "downward" merely describe the configuration shown in the figures. It is understood that the components may be oriented in any direction and the terminology, therefore, should be understood as encompassing such variations unless specified otherwise.

Barbed sutures and placement methods suitable for use according to the methods of the present invention are described in U.S. Pat. No. 5,342,376, entitled "Inserting Device for a Barbed Tissue Connector", U.S. Pat. No. 5,931,855, entitled "Surgical Methods Using One-Way Suture", U.S. Pat. No. 6,241,747, entitled "Barbed Bodily Tissue Connector", U.S. Pat. No. 6,599,310, entitled "Suture Method", U.S. patent application Ser. No. 10/065,256, entitled "Suture Method", issued as U.S. Pat. No. 7,056,331 on Jun. 6, 2006, U.S. patent application Ser. No. 10/065,278, entitled "Barbed Suture in Combination with Surgical Needle", now abandoned, U.S. patent application Ser. No. 10/065,279, entitled "Barb Configurations for Barbed Sutures", issued as U.S. Pat. No. 8,100,940 on Jan. 24, 2012, and U.S. patent application Ser. No. 10/065,280, entitled "Barbed Sutures", issued as U.S. Pat. No. 8,795,332 Aug. 5, 2014. The contents of U.S. Pat. No. 5,342,376, U.S. Pat. No. 5,931,855, U.S. Pat. No. 6,241,747, U.S. Pat. No. 6,599,310, U.S. patent application Ser. Nos. 10/065,256, issued as U.S. Pat. No. 7,056,331 on Jun. 6, 2006, U.S. patent application Ser. No. 10/065,278, now abandoned, U.S. patented application Ser. No. 10/065,279, issued as U.S. Pat. No. 8,100, 940 on Jan. 24, 2012, and U.S. patent application Ser. No. 10/065,280, issued as U.S. Pat. No. 8,795,332 Aug. 5, 2014, are hereby incorporated by reference.

Figure 1:
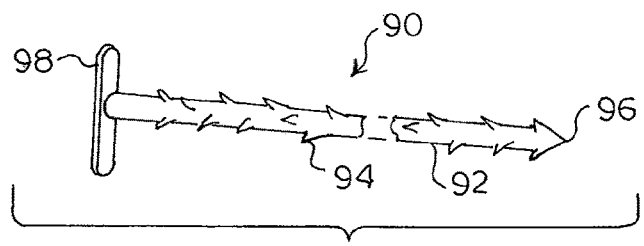
FIG. 1 is a perspective view of an embodiment of a barbed suture with an anchor for use according to the methods of the present invention.
Figure 2:
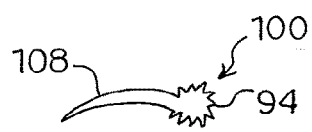
FIGS. 2-11 are end views of embodiments of barbed sutures with anchors according to the present invention.
Figure 3:
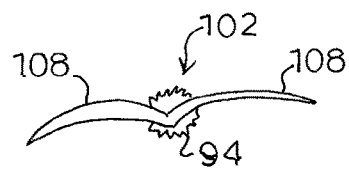
Figure 4:
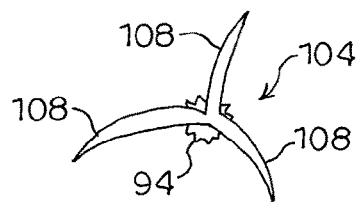
Figure 5:
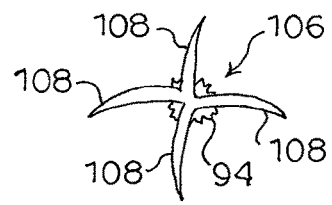
Figure 6:
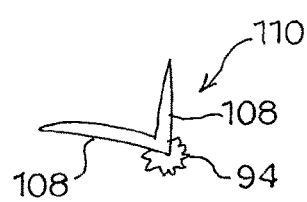
Figure 7:
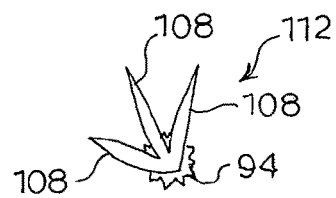
Figure 8:
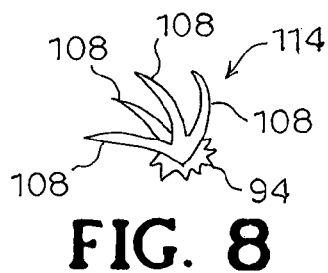
Figure 9:
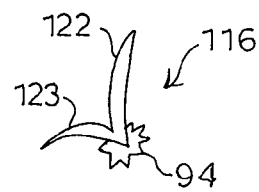
Figure 10:
Figure 11:
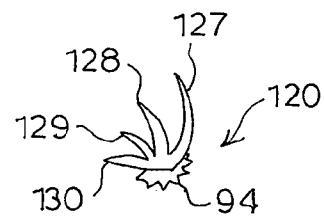

Referring now to the drawings, wherein like numerals designate corresponding or similar elements throughout the several views, FIG. 1 is a perspective view of a single-directional barbed suture 90 having a suture body 92 with barbs 94 extending from around the periphery thereof, a pointed end 96, and an anchor 98 at the other end. The anchor 98 comprises a bar which extends radially outwardly of the suture body 92 in a plane substantially perpendicular to the longitudinal axis of the suture body 92, which generally gives the barbed suture 90 a "T" shape. Many other shapes and configurations of anchors are feasible, as shown in the embodiments in end view (with the suture body normal to and into the page) in FIGS. 2-11. Each of the anchors shown in FIGS. 2-11 have limbs which extend radially outwardly from the suture body 92 a greater distance than the barbs 94. The anchors 98 on the barbed sutures 100, 102, 104, 106 depicted in FIGS. 2-5, respectively, have one or a plurality of limbs 108 generally evenly spaced around the periphery at the end of the suture. The embodiments of the barbed sutures 110, 112, 114 shown in FIGS. 6-8 have anchors 98 including a plurality of limbs 108 which extend from only a portion of the periphery at the end of the suture body 92. FIGS. 9-11 show embodiments of the barbed sutures 116, 118, 120 wherein each of the respective limbs 122-123, 124-126, 127-130 are of different lengths.

Figure 12:
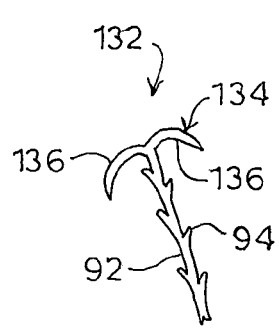
FIGS. 12-20 are elevation views of embodiments of barbed sutures with anchors according to the present invention.
Figure 13:
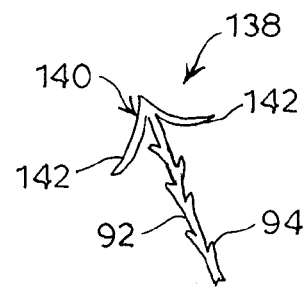
Figure 14:
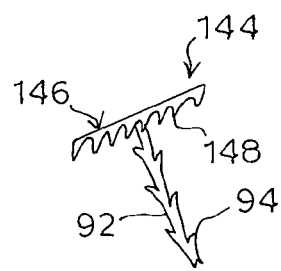
Figure 15:
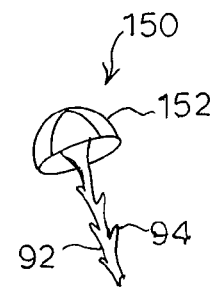
Figure 16:
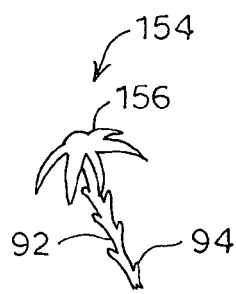
Figure 17:
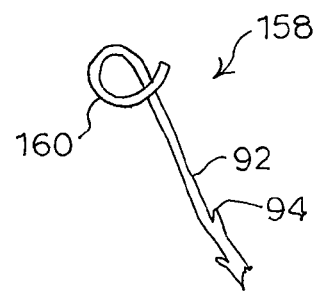
Figure 18:
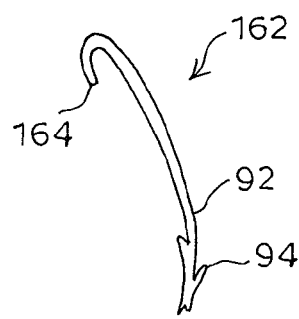
Figure 19:
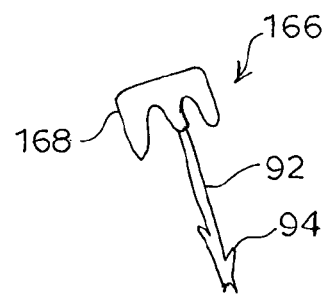
Figure 20:
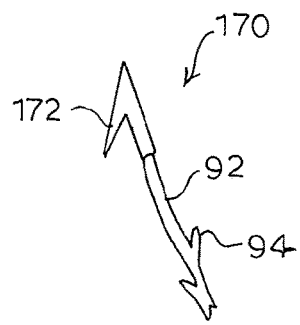

FIGS. 12-20 are further embodiments of barbed sutures at one end. FIG. 12 shows a barbed suture 132 that has an anchor 134 having limbs 136 that are concave toward the other end of the suture. FIG. 13 shows a barbed suture 138 with an anchor 140 having limbs 142 that are concave away from the pointed end of the suture. FIG. 14 shows a barbed suture 144 with an anchor 146 as shown in FIG. 1, further including a plurality of segments 148 extending from the bar toward the other end of the suture. FIG. 15 shows a barbed suture 150 having a hemispherical anchor 152. FIG. 16 shows a barbed suture 154 having an anchor 156 that resembles a coneflower. FIG. 17 shows a barbed suture 158 having an anchor 160 formed by a loop of the body 92 that crosses itself to form a clip, wherein tissue may be received between the clip. FIG. 18 shows a barbed suture 162 having an anchor 164 formed by a hook of the suture body 92. FIG. 19 shows a barbed suture 166 having an anchor resembling an "M" wherein the body 92 of the suture extends from the middle leg of the "M". FIG. 20 shows a barbed suture 170 having a single barb 172, larger than the opposing barbs 94, extending towards the other end of the suture 170. As demonstrated by the variety of anchor designs of FIGS. 12-20, many anchor designs are possible for use with the barbed suture and within the scope of the present invention.

Figure 21:
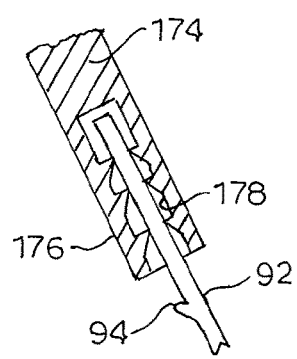
FIG. 21 is an elevation view of a conventional means for affixing a suture to an attachment.
Figure 22:
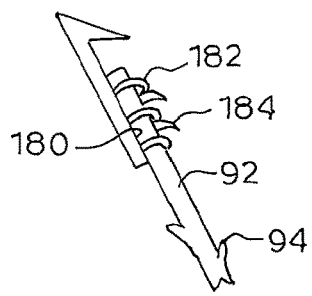
FIGS. 22 and 23 are elevation views of means for affixing sutures to anchors in accordance with the present invention.
Figure 23:
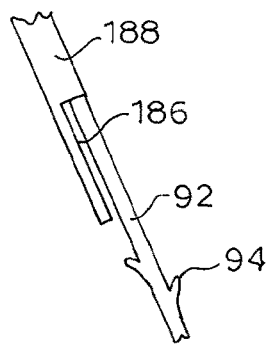

The anchors shown in FIGS. 1-20 may be integrally formed with the body 92 of the barbed suture or, alternatively, may be mounted to the end of the suture. FIGS. 21-23 demonstrate ways that the anchors may be affixed to the barbed sutures. FIG. 21 shows the anchor 172 of FIG. 20. The end of the anchor 172 has an axial bore 178. Teeth 176 are provided on the inside of the bore 178 and angled inwardly. The suture body 92 is inserted into the bore 178 and the end of the anchor 172 is crimped around the suture body 92. FIG. 22 shows the anchor 172 including a plurality of spaced rings 182 on the end of the suture body 92. The end of the suture body 92 is inserted through the rings 182. Barbs 184 are provided on the suture body 92 that oppose the rings 182 and secure the suture body 92 in place by engaging the rings 182. FIG. 23 shows a connection 186 between the anchor 188 and barbed suture body 92 made with, for example, glue or heat.

Figure 24:
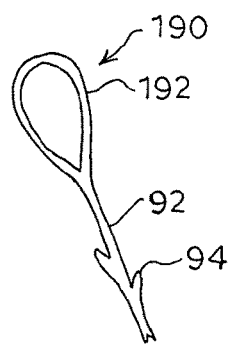
FIGS. 24 and 25 are elevation views of a suture having a looped end according to the present invention.
Figure 25:
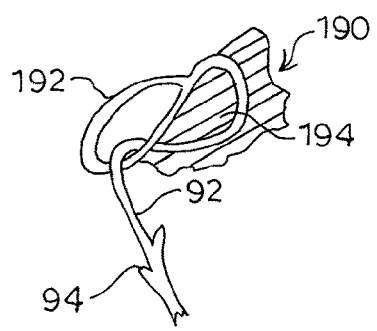

FIG. 24 shows a suture 190 having a loop 192 at one end. Referring to FIG. 25, the suture 190 is placed in tissue 194 by passing the suture 190 through tissue 194 and then through the loop 192. Tissue 194 is trapped by the suture 190 and the loop 192 resulting in the suture 190 being anchored. Optionally, the barbs may be staggered, where the term staggered as used herein in relation to the disposition of barbs on a suture is intended to mean that the suture has at least two sets of barbs that are offset with respect to each other, where the first set is aligned longitudinally on the suture and the second set is aligned longitudinally on the suture, but a plane perpendicular to the suture and cutting transversely through the suture and intersecting the base of a barb of the first set will not intersect the base of a barb of the second set.

The anchors according to the present invention may be formed by stamping and drilling, injection molding, or a laser cutting system, or other method as selected by one of ordinary skill in the art. The anchors may be made of bio-absorbable material, or a material as selected by one of ordinary skill in the art.

Various bio-absorbable polymers include, but are not limited to, polydioxanone, polylactide, polyglycolide, polycaprolactone, and copolymers thereof. Commercially available examples are polydioxanone (sold as PDS II, a trade name used by Ethicon for selling surgical sutures), copolymer of about 67% glycolide and about 33% trimethylene carbonate (sold as MAXON®, a trademark registered to American Cyanamid for surgical sutures), and copolymer of about 75% glycolide and about 25% caprolactone (sold as MONOCRYL®, a trademark registered to Johnson & Johnson for sutures and suture needles). Barbed sutures made from such bio-absorbable materials are useful in a wide range of applications.

Additionally, anchors may be formed from a non-absorbable material, which may be a polymer. Such polymers include, but are not limited to, polypropylene, polyamide (also known as nylon), polyester (such as polyethylene terephthlate), polytetrafluoroethylene (such as expanded polytetrafluoroethylene, sold by Gore as GOR-TEX®), polyether-ester (such as polybutester, which is the condensation polymerization of dimethyl terephthlate, polytetramethylene ether glycol, polymers having ester units (such as polyglycolide), and 1,4-butanediol, and which is marketed by Davis & Geck and by U.S. Surgical, companies owned by Tyco, under the name NOVAFIL®, which is a trademark registered to American Cyanamid for surgical sutures), or polyurethane. Alternatively, the non-absorbable material may be metal (e.g., steel), metal alloys, natural fiber (e.g., silk, cotton, et cetera), and the like.

As used herein, the term wound means a surgical incision, cut, laceration, severed tissue, or accidental wound in human skin or other bodily tissue, or other condition where suturing, stapling or the use of another tissue connecting device might be required.

FIGS. 26-39B show a variety of methods of suture placement in tissue for approximating the sides of wounds or separated tissue according to several embodiments of the present invention. The methods of suture placement include one or more terminal J-stitches, S-stitches, or the like. A terminal J-stitch, S-stitch, or the like comprises a suture placement method wherein a portion of the end of the suture extends in a different direction relative to the adjacent portion of the suture. The relative direction of the end portion of the suture may be, for example, at least approximately 30 degrees from the projected path of the adjacent portion of the suture. For convenience herein, reference is made to J-stitches and S-stitches, but it is understood that suture placement may differ from J-stitches or S-stitches yet still be within the scope of the present invention. Placement of the suture according to the methods of the present invention may be done either by needles or insertion devices as discussed below. Placement in such patterns may be facilitated by manipulation of tissue in addition to or in place of manipulation of the sharp pointed end of the suture. Tissue may be manually grouped and advanced along the suture in accordance with the present invention as described and shown herein.

Reference is sometimes made herein to pointed ends of a suture. The pointed ends of the suture may be straight or curved. In one embodiment, the pointed ends of the suture may be surgical needles secured at each end of the body of the suture so that the body extends between the shank ends of the two needles. The needles are preferably constructed of stainless steel or other surgical grade metal alloy. The needles may be secured to the suture body by means of adhesives, crimping, swaging, or the like, or the joint may be formed by heat shrinkable tubing. A detachable connection may also be employed such that the needles may be removed from the body of the suture by a sharp tug or pull or by cutting. The length of the needles is selected to serve the type of tissue being repaired so that the needles can be completely removed leaving the suture body in the desired position within the tissue.

Figure 26:
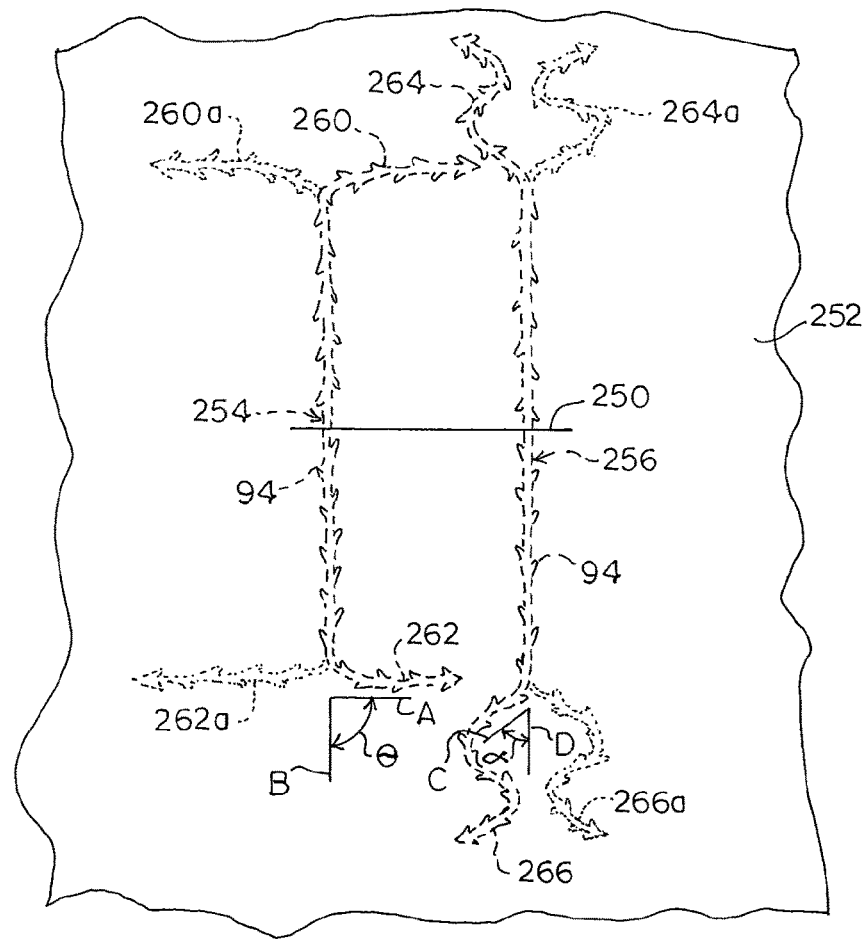
FIGS. 26 and 27 are plan views of embodiments of methods according to the present invention for joining two sides of an open wound in tissue.

In FIG. 26, the sides of a wound 250 in tissue 252 are approximated using two bi-directional barbed sutures 254, 256 having barbs 94. Throughout the figures, solid line sutures indicate the sutures are visible, dashed line sutures indicate the sutures are embedded in tissue, and dotted line sutures indicate an alternative embedded location for the suture. A first suture 254 is positioned using a suture method wherein the two ends are placed in the tissue using a terminal J-stitch 260, 262. A second suture 256 is positioned in the tissue using a suture method wherein the two ends are placed in the tissue using a terminal S-stitch 264, 266. The J-stitches 260, 262 and S-stitches 264, 266 are shown to be pointing in the direction of the other suture, or "inward," but could also be pointed outward in the alternative locations 260a, 262a, 264a, 266a depending on the application and preference of one of ordinary skill in the art. As an example showing the placement of a J-stitch, the end portion of the J-stitch 262 of the first suture 254, aligned along A, is positioned at angle θ from the projected path of the adjacent portion of the suture 254 B, and is shown to be about 90 degrees. As an example showing the placement of an S-stitch, the end portion of the S-stitch 266 of the second suture 256, aligned along C, is positioned at angle α from the projected path D of the adjacent portion of the suture 256, and is shown to be about 45 degrees. The J-stitch and S-stitch angles θ and α may be greater or less than shown and the suture is still considered to be in accordance with the present invention.

Figure 27:
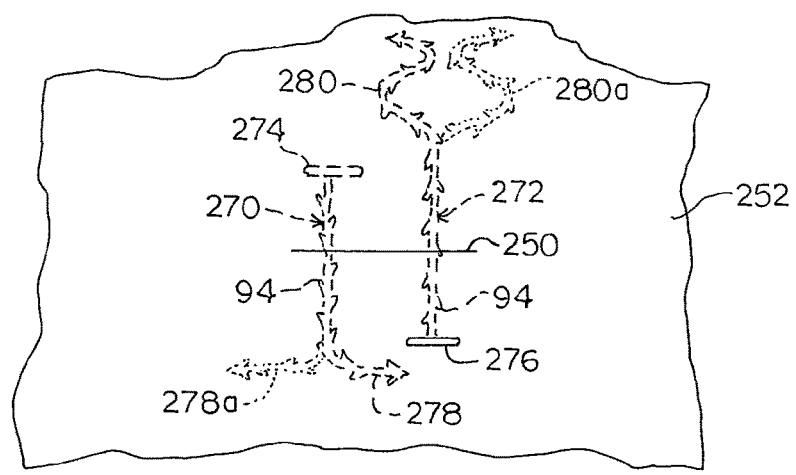

FIG. 27 shows single-directional barbed sutures 270, 272 approximating the sides of a wound 250. Each suture 270, 272 has an anchor 274, 276 and is placed in the tissue 252 using a method which ends with a terminal J-stitch 278 or S-stitch 280 at the opposite end. Alternative J-stitch or S-stitch positions 278a, 280a may be used. Anchors may be embedded in the tissue 252 as with the anchor 274 of a first suture 270 by making a small incision, or may be above the tissue as with the anchor 276 of a second suture 272. The sutures 270, 272 may be placed with a sharp pointed end such as a needle at the opposite, leading end of the suture from the anchors 274, 276. The anchors 274, 276 are shown schematically; it is understood that a variety of anchors is available as appropriate, as previously discussed.

For convenience in the remaining embodiments described herein, mostly J-stitches are shown. It should be understood, however, that in all embodiments shown herein that have a suture placed with a needle, S-stitches could replace any depicted J-stitches. In one method of grouping and advancing tissue along the suture body, the sharp pointed end of the suture exits the tissue prior to completing, for example, the J-stitch. Then the tissue is grouped and advanced along the suture body, and then the suture pointed end enters the tissue to complete the J-stitch.

Figure 28:
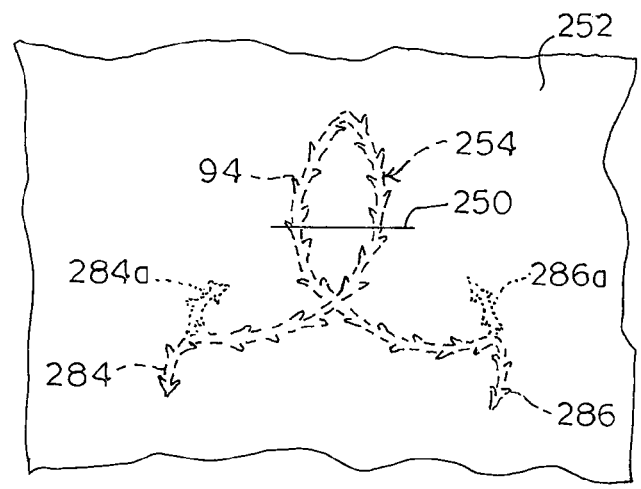
FIGS. 28 and 29 are plan views of embodiments of methods according to the present invention for joining two sides of an open wound in tissue
Figure 29:
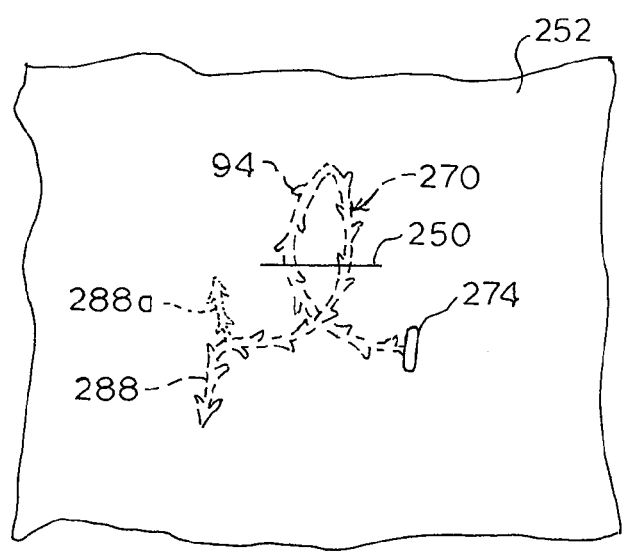
Figure 30:
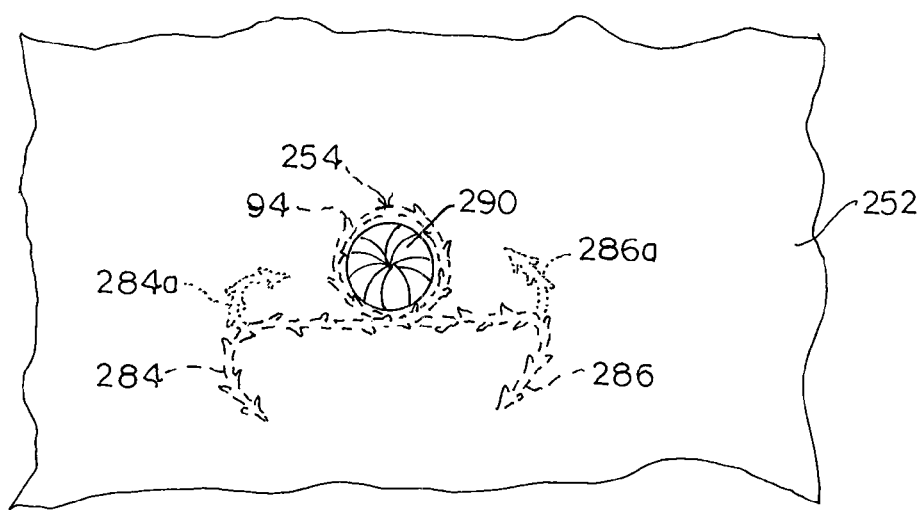
FIGS. 30 and 31 are plan views of embodiments of methods according to the present invention for inverting a surface wound in tissue.
Figure 31:
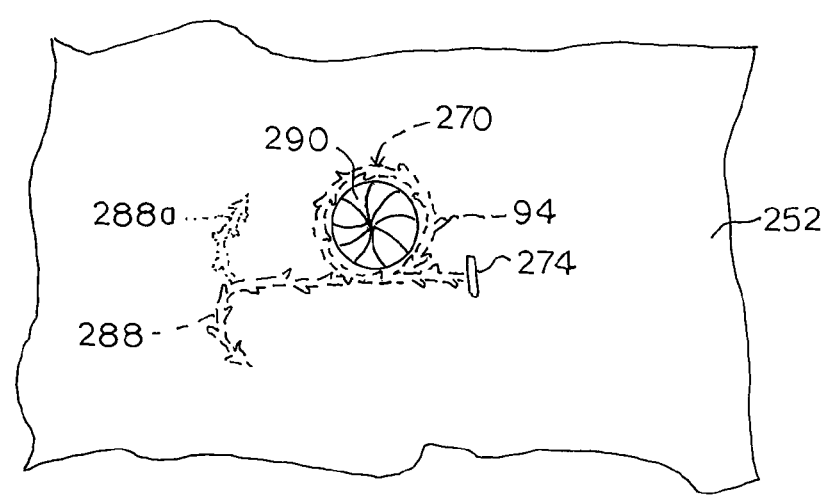

FIGS. 28 and 29 show suture methods using an alpha stitch pattern using a bi-directional barbed suture 254 and a single direction suture 270, respectively, to close a wound 250. The suture method using the bi-directional barbed suture 254 of FIG. 29 has a J-stitch at each end that may be either downward 284, 286, upward 284a, 286a, or a combination thereof. The suture method using the single direction suture of FIG. 29 has a J-stitch shown at its leading end that may be either downward 288 or upward 288a. A purse-string stitch is a surgical suture method used to repair excisions, such as in as appendectomy, where inverting the remaining tissue is desired. A purse-string stitch may be used according to the methods of the present invention with a bi-directional barbed suture 254 or a single direction suture 270 as shown in FIGS. 30 and 31, respectively. The description of FIG. 28 applies to FIG. 30, and the description of FIG. 29 applies to FIG. 31.

Figure 32:
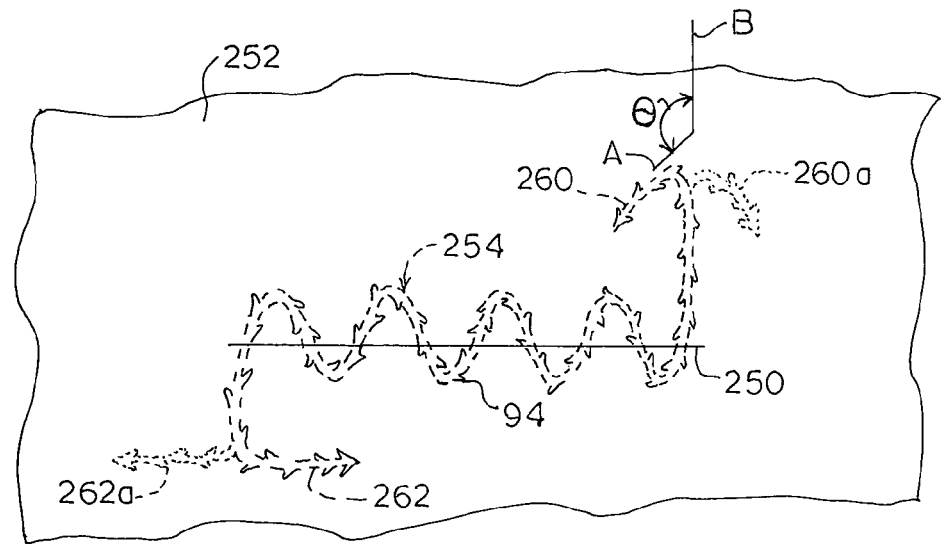
FIGS. 32-39B are plan views of additional embodiments of methods according to the present invention for joining two sides of an open wound in tissue.
Figure 33:
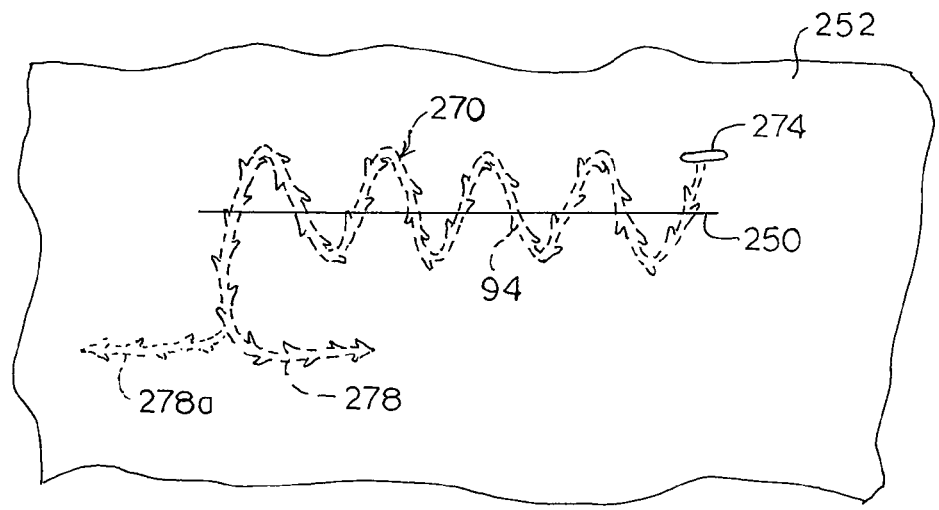

FIGS. 32 and 33 show suture methods using a zig-zag pattern to approximate the sides of a wound 250 with a bi-directional barbed suture 254 and a single-directional barbed suture 270 with an anchor 274, respectively. As previously shown in FIG. 26 and as shown in FIG. 32, the terminal end path A of the end portion of the suture 254 in the J-stitch 262 is at an angle from the projected suture path B of the adjacent portion of the suture. The J-stitch angle shown is about 135 degrees. It is understood that the angle may vary and still be considered a J-stitch.

Figure 34:
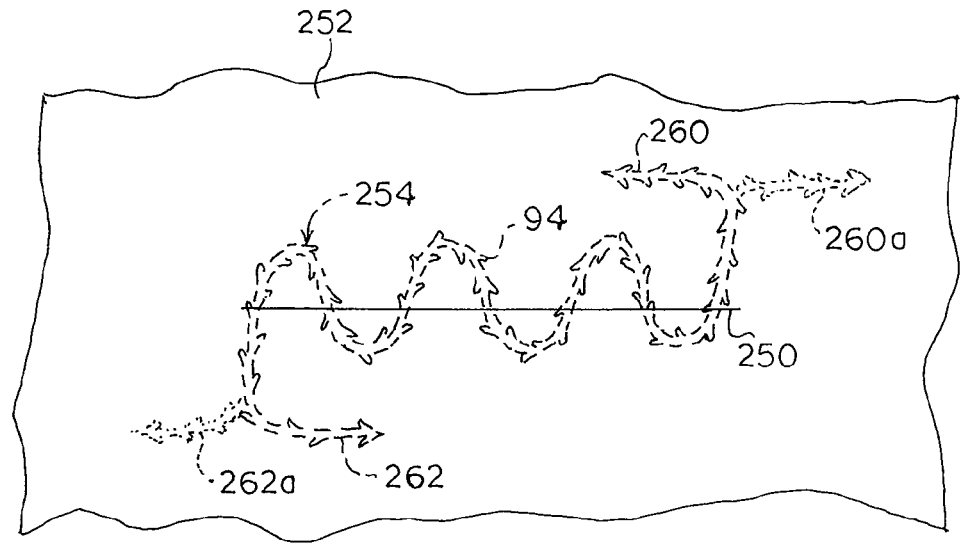
Figure 35:
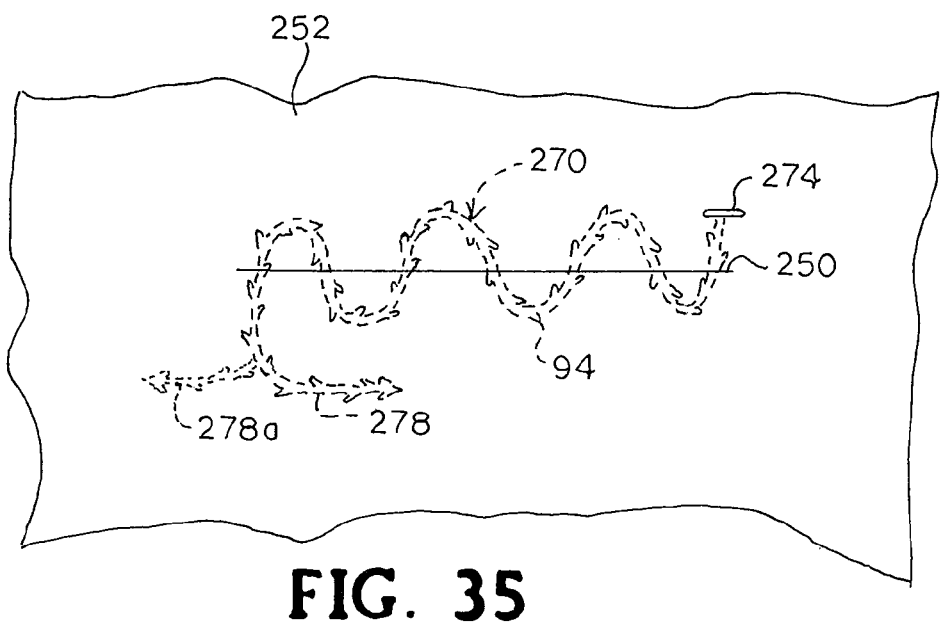

FIGS. 34 and 35 show a suture method for approximating the sides of a wound using a bi-directional barbed suture 254 and a single direction barbed suture 270 with an anchor 274, respectively, placed in the tissue 252 in a sinusoidal pattern.

Figure 36:
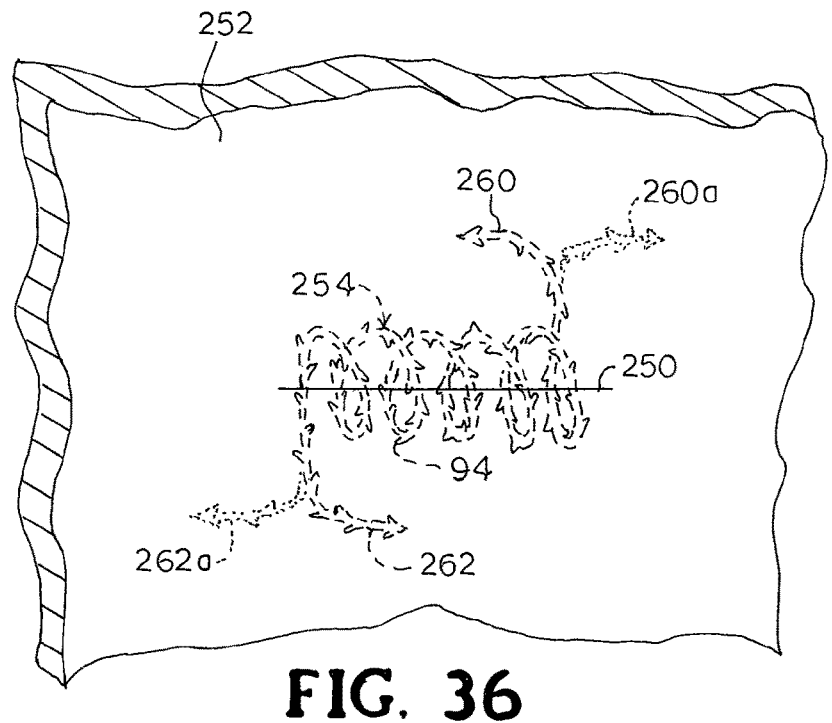
Figure 37:
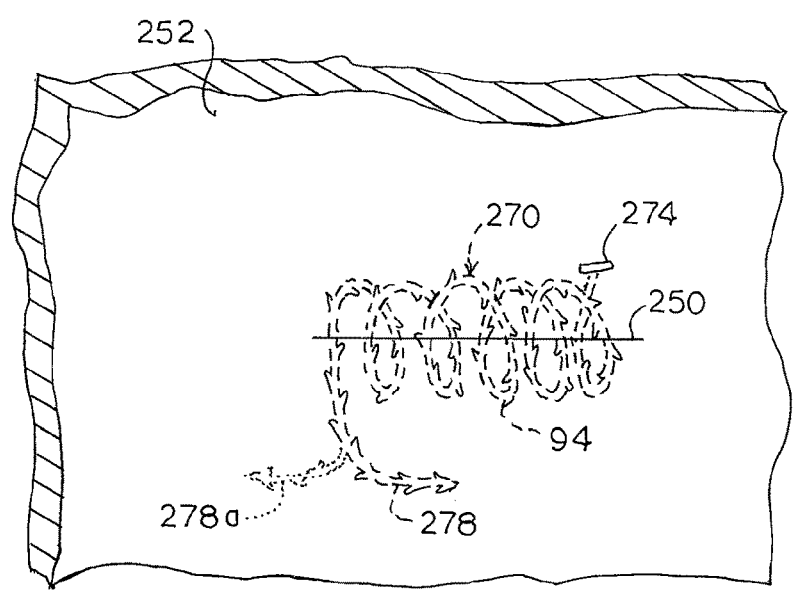

FIGS. 36 and 37 show a bi-directional barbed suture 254 and a single direction barbed suture 270 with an anchor 274, respectively, placed in the tissue 252 in a corkscrew pattern.

With respect to the bi-directional suture 254 of FIGS. 32, 34, and 36, the suturing begins at an intermediate point between the ends of the wound and proceeds in both directions. In the zig-zag and sinusoidal patterns of FIGS. 32 and 34, respectively, the central portion of the suture 254, where the barbs 94 change direction, could also be located at one end of the wound, with both ends of the suture proceeding in the same direction along the wound in separate patterns which are mirror images of one another. Both ends of the suture could then have a J-stitch or S-stitch at the same end of the wound. The J-stitches of FIGS. 32, 34, and 36 may be inward 260, 262, outward 260*a*, 262*a*, or a combination thereof. The J-stitches of FIGS. 33, 35, and 37 may be inward 278 or outward 278*a*. Further, the suture 270 shown in FIGS. 33 and 35 could double back in a mirror image pattern to the end of the wound placing the leading end near the anchor 274, and could have a J-stitch or S-stitch at that location.

The anchors 274 of FIGS. 33, 35, and 37 are shown as contacting the surface of the tissue 252. Another method according to the present invention allows placement of the anchor 274 below the surface of the tissue as shown in FIGS. 38A and 38B.

Figure 38A:
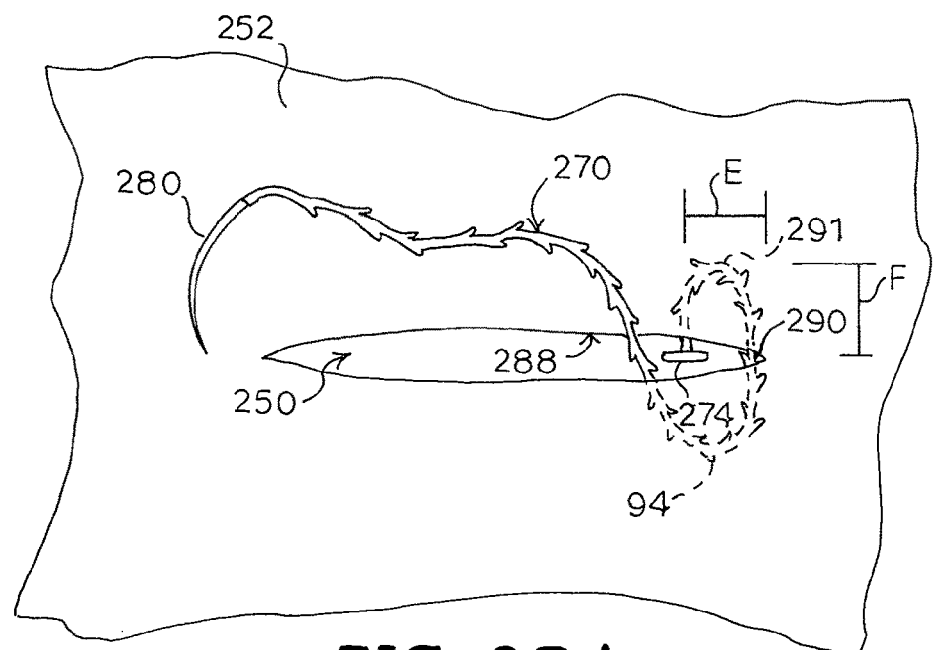
Figure 38B:
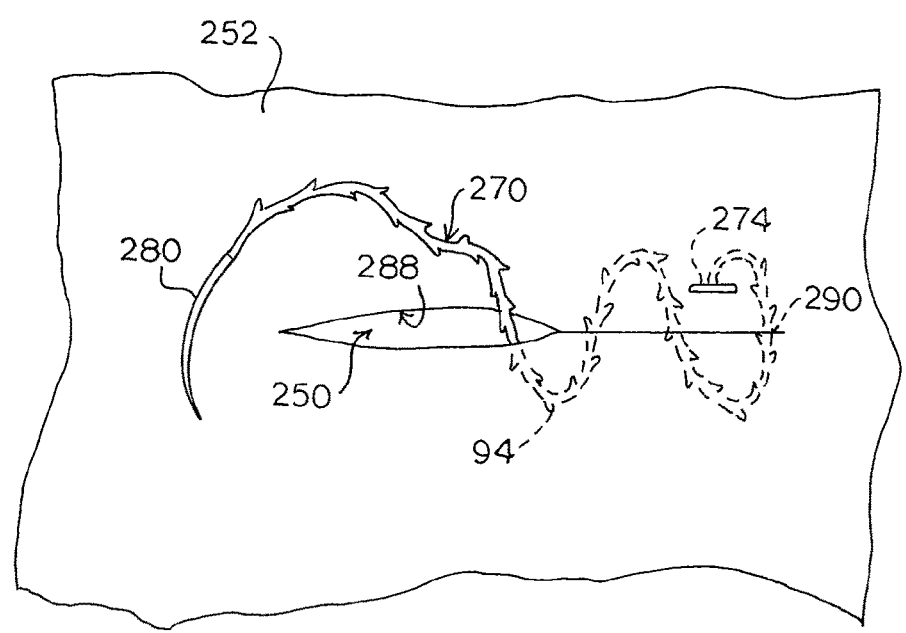

As shown in FIG. 38A, a sharp pointed end of the suture 270, for example, a needle 280, is at the leading end of a single-directional barbed suture 270 and is inserted into a face 288 of a wound 250. As the suture 270 is pulled through the tissue by the needle 280, the anchor 274 will abut the face of the wound 288. As the suture is pulled to approximate the wound, the anchor 274 will move until it meets resistance in the tissue 252. The tissue 252 generally comprises layers that are parallel to the surface of the tissue. Depending on the shape of the anchor 274, the anchor 274 may be expected to move between the layers and past the face 288 of the wound 250, embedding into the adjacent tissue, arriving in a position spaced from the face 288 of the wound 250 as shown in FIG. 38B. Referring to FIG. 38A, in one embodiment, as selected by one of ordinary skill in the art the distance E from the end of the wound to the anchor 74 may be approximately the same as the distance between "bites," or the distance F from the face 288 of the wound to the peak 291 of the pattern.

Figure 39A:
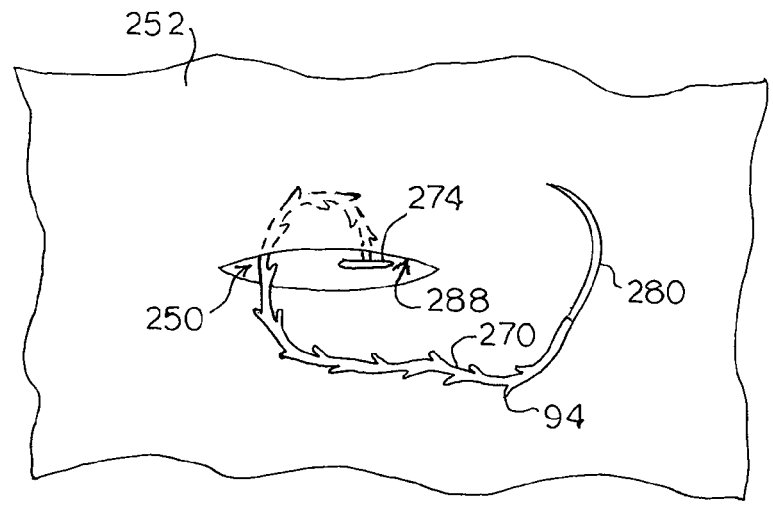
Figure 39B:
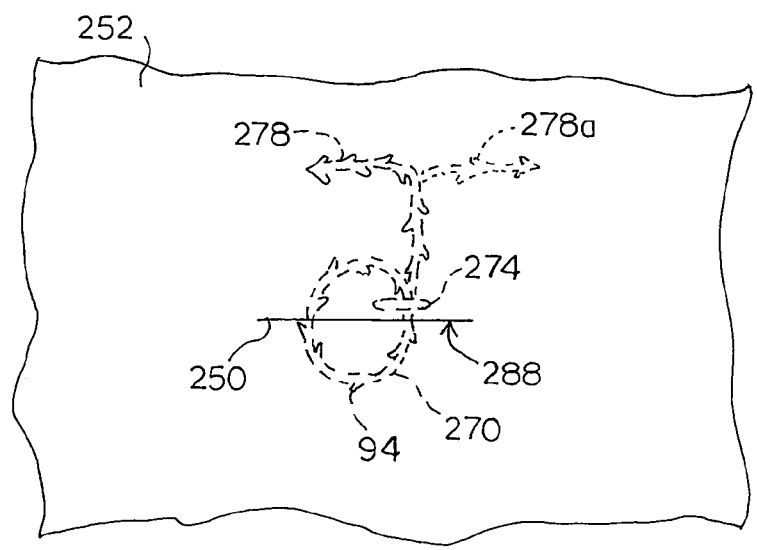

Another suture method using a single directional barbed suture wherein anchors are embedded in tissue is used for approximating a small wound, as shown in FIGS. 39A and 39B. In FIG. 39A, the needle 280 at the leading end of a single-directional barbed suture 270 is inserted into the face 288 of a wound 250. Similarly to the method shown in FIGS. 38A and 38B, as the suture 270 is pulled by the needle 280, the anchor 274 will abut the face 288 of the wound 250. As the suture is pulled to approximate the sides of the wound 250, the anchor will move into the tissue 252 until it meets resistance in the tissue 252. In FIG. 39B, the anchor is shown to have moved into final position spaced from the wound face 288. The placement of the suture 270 may form a loop, and the leading end may be placed as a J-stitch with alternative configurations 278, 278*a*.

Figure 40:
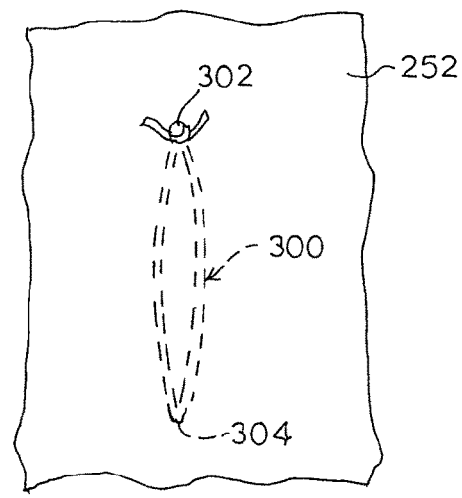
FIGS. 40 and 41 are plan views of conventional methods for positioning tissue.
Figure 41:
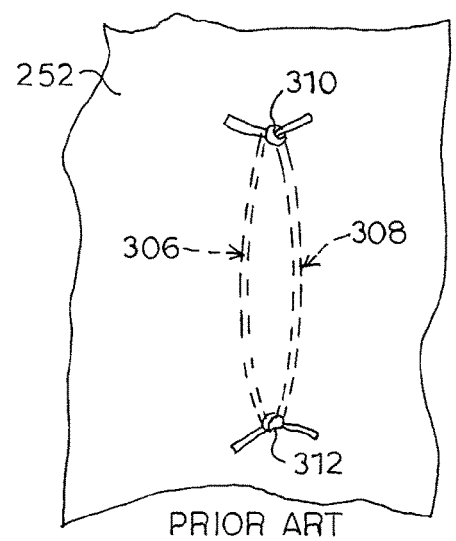

FIGS. 40-50 show suture method according to the present invention wherein barbed sutures are placed to position tissue where there is no wound and the sutures are below the surface of the tissue, such as in cosmetic surgery. FIGS. 40 and 41 show the placement conventional, non-barbed sutures in tissue for providing lift. The method of FIG. 40 uses one suture 300 with one knot 302 at the top and an exit/entry point 304 at the bottom. The knot is tightened to adjust the tissue 252 to the desired amount of lift. The method of FIG. 41 uses two sutures 306, 308 with one knot 310 at the top and another knot 312 at the bottom. The knots are tightened to provide the desired amount of lift to the tissue 252. The force sufficient to provide tissue lift is applied at the knots 302, 310, 312, and the load on the tissue 252 is concentrated at the top knots 302, 310 and bottom knot 312 or low point 304 of the sutures.

Figure 42:
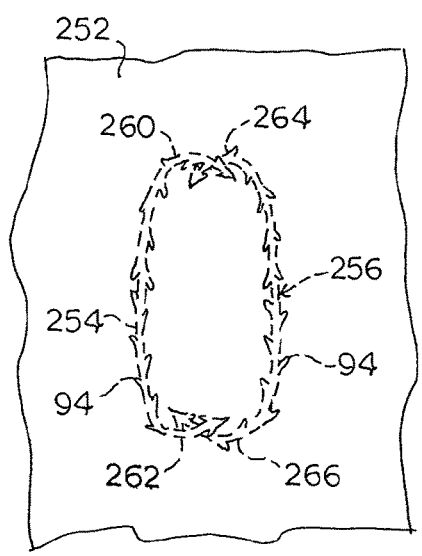
FIGS. 42-45 are plan views of embodiments of methods according to the present invention for positioning tissue relative to a barbed suture disposed in the tissue.
Figure 43:
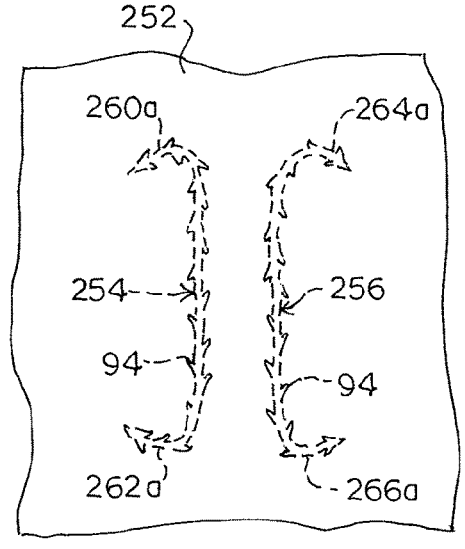
Figure 44:
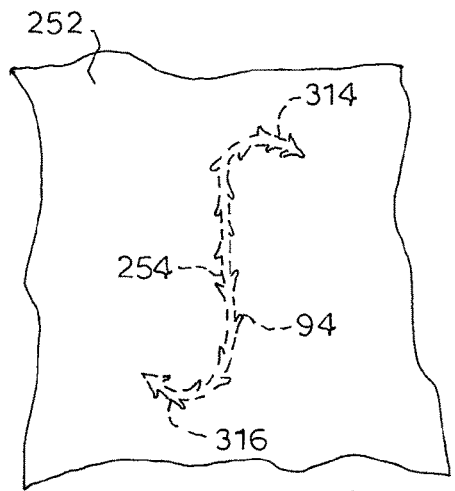

FIG. 42 shows a suture method according to the present invention wherein bi-directional barbed sutures 254, 256 are placed substantially parallel to one another and having J-stitches 260, 262, 264, 266 at each end that are directed toward the adjacent suture, or inward. FIG. 43 shows a similar suture method using two parallel bi-directional barbed sutures 254, 256 with the J-stitches 260*a*, 262*a*, 264*a*, 266*a* directed outwardly. FIG. 44 shows a bi-directional barbed suture 254 with terminal J-stitches 314, 316 extending in opposite directions. Once the sutures 254, 256 are placed, the tissue may be manually advanced along each suture to be grouped as desired by the surgeon for a certain amount of tissue lift. Unlike the conventional methods of FIGS. 40 and 41, the resistance provided by the barbed sutures is distributed along the length of the suture.

Figure 45:
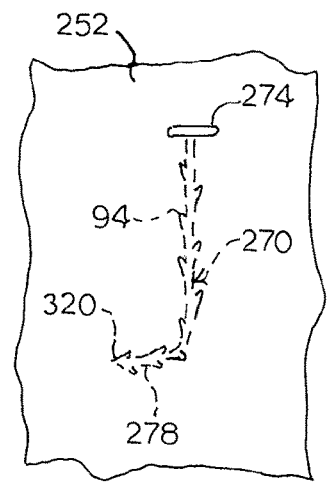

FIG. 45 shows an embedded single-directional barbed suture 270 having an anchor 274 and a pointed end 320 positioned below the surface of the tissue 252 and terminating in a J-stitch 278. Optionally the J-stitch 278 may be oriented differently or omitted altogether.

Figure 46:
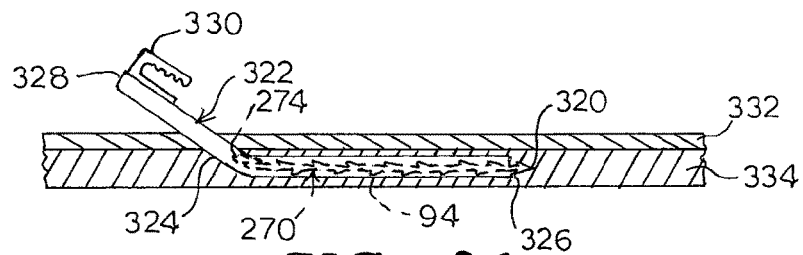
FIGS. 46-48 are section views of embodiments of methods according to the present invention.
Figure 47:
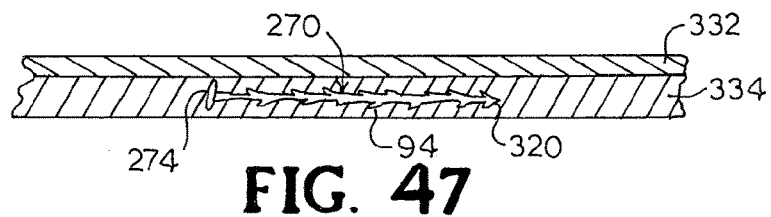
Figure 48:
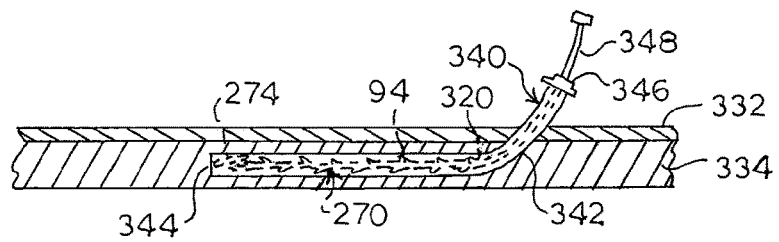

One method of placing a single-directional barbed suture 270 below the surface of tissue 252 is with an insertion device. Insertion device designs include straight, curved, and corkscrew. One such method of using an insertion device 322 is shown in FIG. 46. The insertion device 322 may include a straight or curved tube 324, a leading end 326, a trailing end 328, and a handle 330 for ease of use. Some nonlinear suture installations may be performed with a straight tube by manipulation of tissue rather than with a curved tube. The pointed end 320 of the suture 270 may extend from the leading end 326 of the insertion device 322 or from an opening (not shown) in the side of the insertion device 322. At least one barb 94 on the suture 270 must extend through the opening at the leading end 326 or through the opening at the side of the insertion device. Alternatively, an anchor 274 could extend through the opening at the leading end 326 or through the opening at the side of the insertion device. The insertion device 322 is advanced through the epidermis 332 and into subcutaneous tissue 334. When in the desired position, the insertion device 322 is withdrawn by the trailing end 328, and the pointed end 320 and barbs 94 of the suture 270 engage in the subcutaneous tissue 334, leaving the suture 270 in place to restrict movement in one direction as shown in FIG. 48. The anchor 274 is also embedded, restricting movement in the other direction.

Another method of placing a single-directional barbed suture 270 with an insertion device is shown in FIG. 48. The insertion device 340 has a straight or curved tube 342, a leading end 344, a trailing end 346, and a reciprocating plunger 348. The anchor 274 is disposed in the tube 342 adjacent the leading end 344 of the insertion device 340. The insertion device 340 is advanced through the epidermis 330 and into the subcutaneous tissue 334. When in the desired position, the plunger 348 is depressed until the anchor 274 is expelled from the tube 342 and into the subcutaneous tissue 334. As the insertion device 340 is withdrawn from the trailing end 346, the anchor 274 engages in the tissue to restrict movement in one direction. The barbs 94 also engage of the subcutaneous tissue 334, restricting movement in the opposite direction.

The anchor 274 may be any design that fits within the insertion device, and may include collapsing designs that are collapsed while within the insertion device tube and expand when released. A "T" shape design is shown in the figures for convenience, and may be used when configured to fold along the direction of the insertion device tube. Further, the methods illustrated in FIGS. 45-48 and described above may also be used to place single-directional barbed sutures with an insertion device to approximate the sides of a wound, as shown in FIG. 27.

Figure 49:
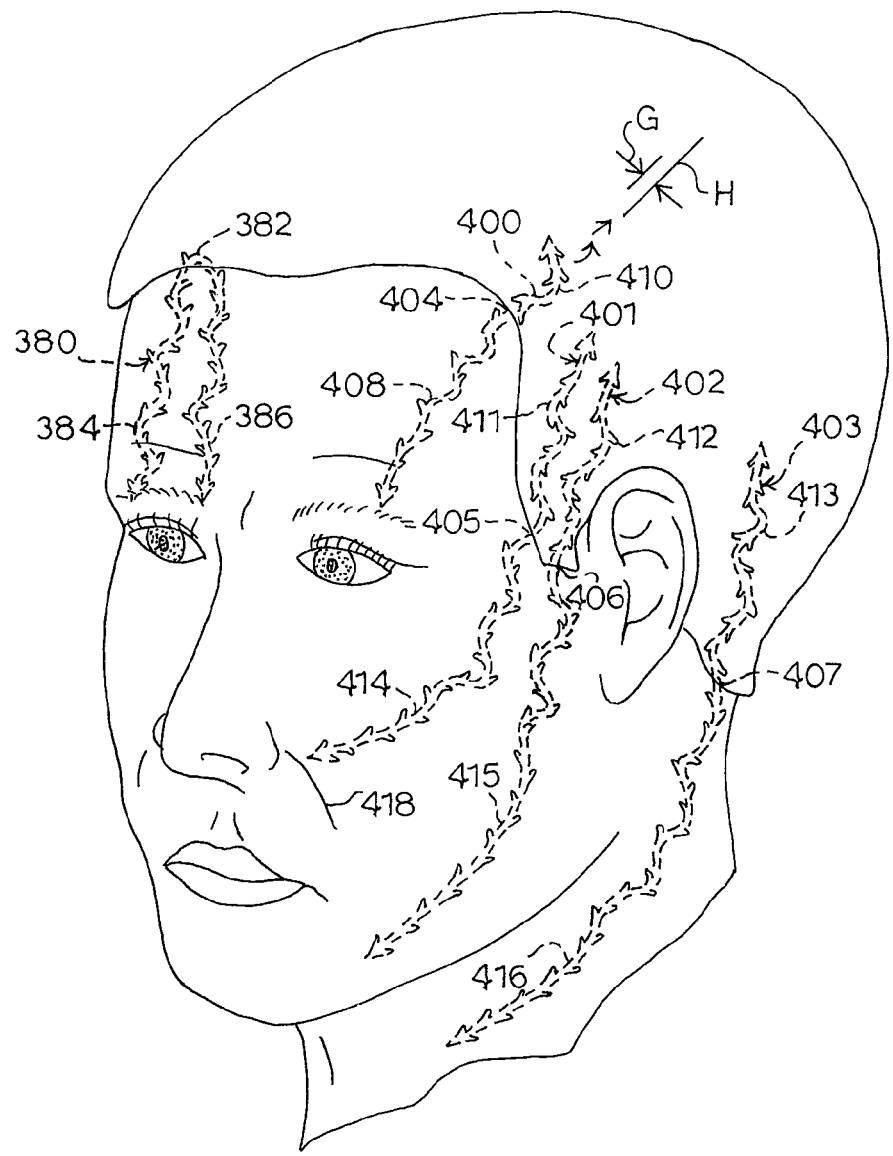
FIGS. 49 and 50 are plan views of further embodiments of methods according to the present invention for positioning tissue along a barbed suture disposed in the tissue.

FIG. 49 shows placement of five bi-directional barbed sutures 380, 400-403 using methods for cosmetic lifts for the brow, face, and neck according to the present invention. Each of the five bi-directional barbed sutures 380, 400-403 shown may be placed, in one embodiment, using a straight needle at each end. For a brow lift, the ends of the suture 380 forming an inverted "U" or "V" shape, or variations thereof, enter at the same insertion point 382, generally superior to the hairline (or where the hairline would be expected). Sutures 400-403 may be placed with the ends extending in generally opposite directions starting from an insertion point 404-407 that may generally be superior to the expected hairline and exiting distally. In all methods, a side-to-side motion with the needle is used, in one embodiment without exiting the tissue until terminating, for placing the suture in a sinusoidal pattern. The sinusoidal pattern may have greater or lesser amplitudes and frequencies than those shown in FIG. 49 and be within the scope of the present invention. As an alternative to bi-directional barbed sutures 380, 400-403, single-directional barbed sutures could be used for each portion 384, 386, 408, 410-416 of the respective sutures and their ends tied at the insertion points 382, 404-407 to the adjacent suture. Further, there may be generally straight portions of placed suture between the curvilinear portions and exit points. Following placement of a suture, tissue is advanced and grouped along the body of the suture for providing lift and tissue support.

Placement of a suture in a sinusoidal pattern increases the suture's "shock-absorbing" capability and provides multiple opportunities for the suture to elongate or straighten and prevent shifted or repositioned tissue from relapsing (moving toward its original position). The amplitude of the curvilinear pattern is generally perpendicular to the direction of the resultant holding force of the suture, which is generally along the axis of the curvilinear pattern. An example amplitude is shown at G in FIG. 49 and an example resultant holding force is shown at H. Pulling of the tissue may cause the tissue to relapse more than with straight-placed sutures, but there may be less breakage of the sinusoidally placed sutures because of the flexure provided by the sinusoidal pattern. The sinusoidal pattern may permit larger or tighter lifts as compared to the same number and size of sutures that are linearly placed. The sinusoidal pattern may also allow the use of fewer and bigger sutures, which may be desirable when the patient does not want to be sedated.

For the browlift sutures 380, 400 and other lifts on the forehead, the portion 384, 386, 408 of the suture in the forehead engages just above muscle, frontalis, in subepidermal tissue. Subepidermal tissue includes the papillary dermis, reticular dermis, and subcutaneous tissue. The portions 410-413 of the sutures 400-403 extending into the scalp engage the galea aponeurotica and subepidermal tissue.

In general, for the sutures 401-403 in the face and neck, the anterior portions 414-416 engage just above muscle, platysma, but are slightly more superficial in the cheek or near the nose, and in subepidermal tissue. In particular, the anterior portion 414 of the facelift suture 401 in the upper face extends toward the nasolobial fold 418, engaging the subepidermal tissue, superficial muscular aponeurotic system, or both.

Specifically with respect to the facelift suture 402 in the cheek, the insertion point 406 is approximately at the posterior mandibular angle. The first end 412 of the suture is pushed posterially through subepidermal tissue, the superficial aponeurotic system, or combinations thereof along a path approximately parallel to the mandibular border, exiting distally. The second end 415 of the suture is pushed anteriorly through subepidermal tissue, the superficial aponeurotic system, or combinations thereof along a path approximately parallel to the mandibular border, also exiting distally.

For the surgical procedure comprising a neck lift, the insertion point 407 of the barbed suture 403 is approximately at the upper sternomastoid muscle. The first end 413 of the suture is pushed posterially through subepidermal tissue, the superficial aponeurotic system, or combinations thereof along a path approximately parallel to the mandibular border, exiting distally. The second end 416 of the suture is pushed anteriorly through subepidermal tissue, the superficial aponeurotic system, or combinations thereof along a path approximately parallel to the mandibular border, also exiting distally.

Additional cosmetic surgery applications may be performed within the scope of the present invention. For example, thigh lifts and breast lifts may be performed. In a thigh lift the insertion point is generally at the inguinal crease. The first end of the suture is pushed cranially through subepidermal tissue until the first end of the suture extends out of the tissue, and the second end of the suture is pushed caudally through subepidermal tissue until the second end of the suture extends out of the tissue on the thigh. The thigh tissue is then advanced and grouped along the body of the suture for providing lift and tissue support.

In a breast lift, the insertion point is at the upper aspect of the breast curvature. The first end of the suture is pushed through subcutaneous tissue, dermal tissue, and pectoralis muscle until extending out of the tissue at an exit point on the upper portion of the breast. The second end of the suture is pushed caudally through fibrous and fatty tissues until the second end of the suture extends out of the tissue at an exit point along the anterior aspect or the lower curvature of the breast. The breast tissue is then advanced and grouped along the body of the suture for providing lift and tissue support.

Figure 50:
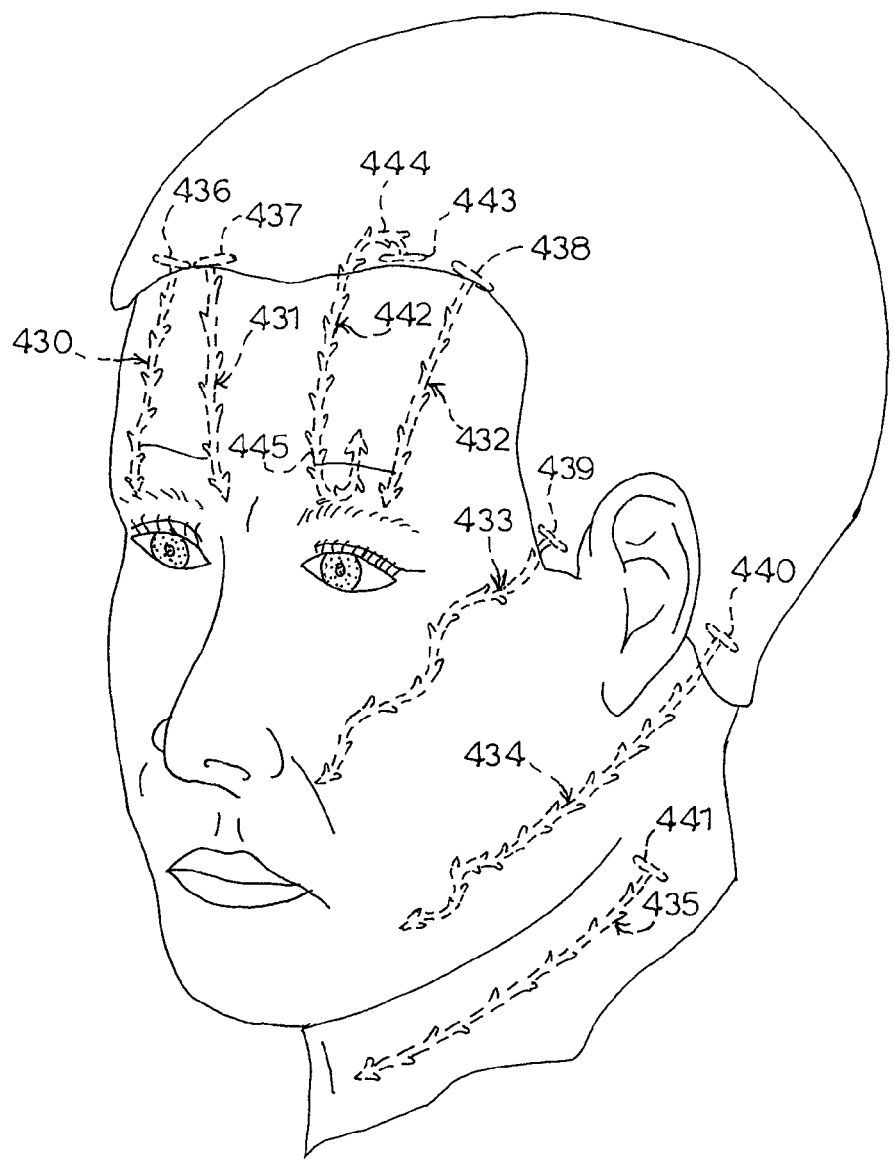

FIG. 50 shows suture methods for cosmetic surgery applications using single-directional barbed sutures 430-435 with anchors 436-441 according to the present invention. These suture methods may optionally include a terminal J-stitch or S-stitch (not shown), and may be placed with an insertion device 322, 340 as shown in FIGS. 46-49 or with a needle. For example, one suture 434 along the jaw line is shown as terminating at its pointed end with an S-stitch. Another suture 433 in the upper face is shown having a curvilinear pattern similar to those of FIG. 49. Although a schematic "T" shape anchor 436-441 is shown, the anchor may be any design as described herein and selected by the surgeon depending on the application. The anchors may be embedded either by use of an insertion device or by making a small incision. Another suture 442 is shown in the forehead and is placed with curves at the ends 444, 445, including a J-stitch proximate to the end 445 at the brow. Applications to brow, face, neck, thigh, and breast are similar to and correspond to those detailed above for bi-directional sutures in similar locations with respect to the tissue engaged. Following placement of the suture, tissue is advanced and grouped along the body of the suture for providing lift and tissue support. As a variation to grouping and advancing the tissue along the suture after completing the desired pattern, such as a J-stitch, the suture pointed end may exit the tissue prior to completing the J-stitch, then the tissue may be grouped and advanced, and then the J-stitch may be completed.

Figure 51A:
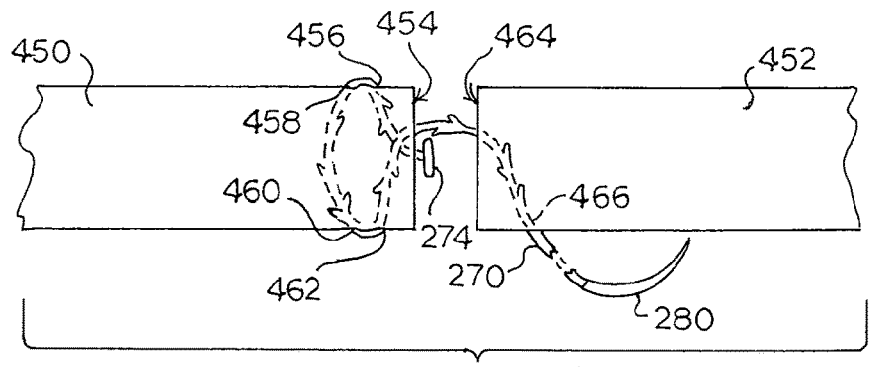
FIGS. 51A-51C are plan views of an embodiment according to the present invention for joining two ends of a severed tendon.
Figure 51B:
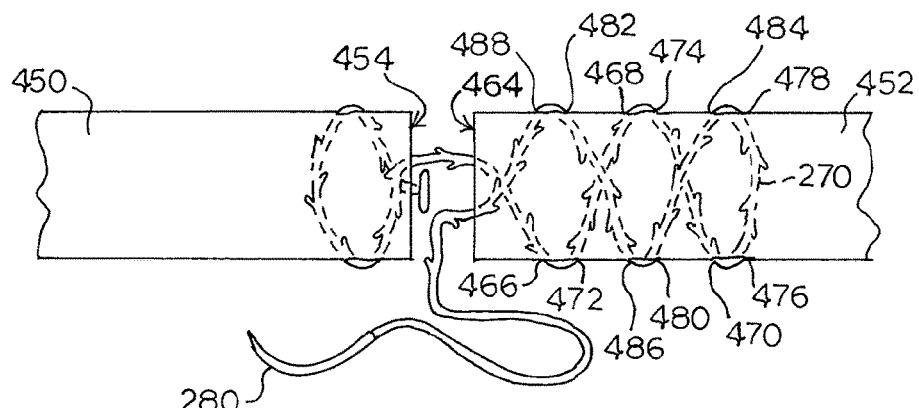
Figure 51C:
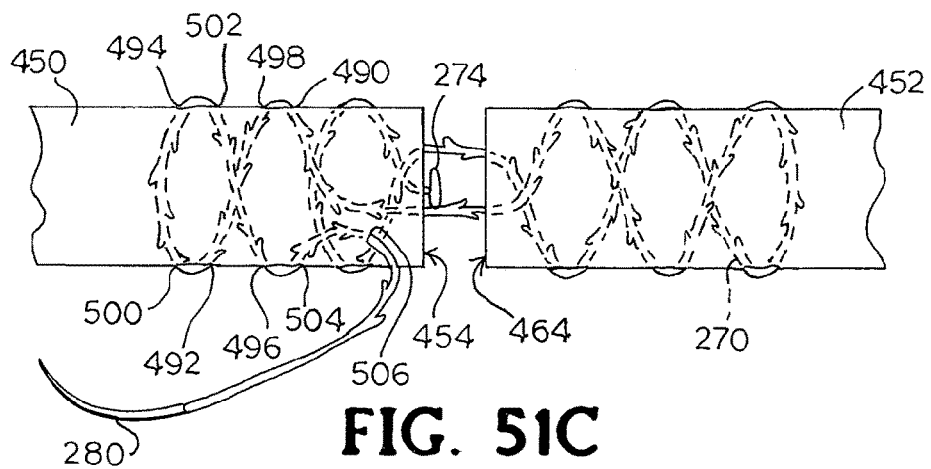

FIGS. 51A-51C show the use of a single-directional barbed suture 270 for repair of two parts of a severed tendon 450, 452, referred to for convenience as the left part 450 and right part 452. As shown in FIG. 51A, the suture enters the end 454 of the left part 450 and follows a curvilinear path to an exit point 456. The anchor 274 abuts the end 454 of the left part 450. The suture enters again at a point 458 adjacent to the exit point 456 and continues to form a loop on the curvilinear path until exiting at point 460 and then entering at point 462. The suture completes the loop and exits through the end 454 of the left part 450 then passes through the end 464 of the right part 452. As shown in FIG. 51B, the suture follows the selected curvilinear path advancing through the tendon 252 away from the end 464 by exiting at points 466, 468, 470 and entering at points 472, 474, 476, and then returns back to the end 464 by exiting the tendon through points 478, 480, 482 and entering through points 484, 486, 488. As shown in FIG. 51C, the suture then again enters the end 454 of the left part 450, follows the selected curvilinear path exiting the tendon at points 490, 492, 494, 496 and entering at points 498, 500, 502, 504 until making a final exit 506 from the periphery of the tendon.

Also according to the present invention, methods are provided for joining the ends of two portions of a tube, a tubular structure, or a hollow organ within the body using a barbed suture, such as the ends of a blood vessel in an anastomosis procedure. As used herein, the term "tube" includes but is not limited to, blood vessels, the large and small intestine, ducts, and the like. As shown in FIGS. 52-55, the ends of the tube may be first cut at an angle prior to joining for promoting a more effective attachment.

Figure 52:
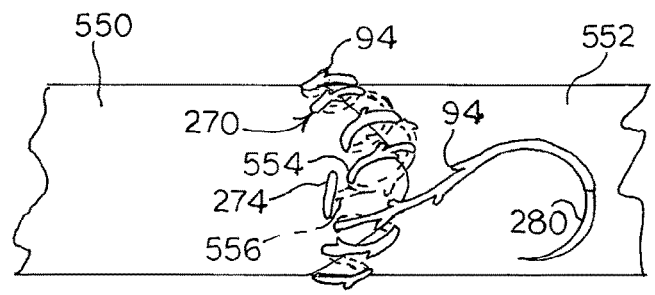
FIGS. 52-55 are plan views of embodiments according to the present invention for joining two bodily tube ends.

Referring to FIG. 52, a method is shown for joining the ends of a tube using a single-directional barbed suture 270 having an anchor 274. The pointed end 280 of the barbed suture 270, which in the embodiment shown comprises a needle, is inserted through the wall and into the interior of a first end 550 of the tube. The pointed end of the suture 270 is then inserted from the interior of the tube through the wall of a second end 552 of the tube. The suture 270 is pulled through the walls of the tube until the anchor 274 contacts the outer surface of the wall of the first end 550 of the tube for drawing the two ends 550, 552 of the tube together. The suture 270 is then again inserted through the wall of the first end 550 of the tube at a point 554 circumferentially spaced from the initial insertion point 556. The steps are repeated for advancing the suture 270 around the tube. After the last bite, the suture pattern may be completed with a terminal J-stitch or S-stitch.

Figure 53:
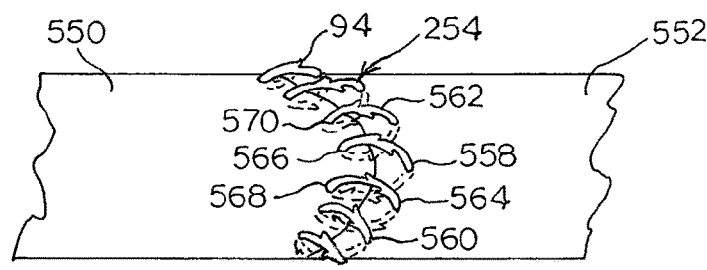

FIG. 53 shows a method of using a bi-directional barbed suture 254 for joining the ends 550, 552 of a tube using a similar suture pattern as the method shown in FIG. 52. Beginning at an initial insertion point 558, an end of a first portion 560 of the suture 254 is inserted through the wall and into the interior of a first end 552 of the tube. The end of the first portion 560 of the suture 254 is then inserted from the interior of the tube through the wall of a second end 550 of the tube. The first portion 560 of the suture 254 may be pulled through the walls of the tube until the opposed barbs on a second portion 562 of the suture 254 contact the outer surface of the wall of the first end 552 of the tube for drawing the two ends 550, 552 of the tube together. The end of the first portion 560 of the suture 254 is inserted through the wall and into the interior of the first end 552 of the tube at a point 564 circumferentially spaced in a first direction from the initial insertion point 558. The end of the second portion 562 of the suture 254 is inserted through the wall and into the interior of the second end 550 of the tube at a point 566 circumferentially spaced from the exit point 568 of the end of the first portion 560 of the suture 254. The end of the second portion 562 of the suture 254 is then inserted from the interior of the tube through the wall of the first end 552 of the tube at a point 570 circumferentially spaced in a second direction from the initial insertion point 558. These steps are repeated for advancing each end of the barbed suture 254 around the tube. After the last bite, the suture pattern may be completed with a terminal J-stitch or S-stitch at each end.

Figure 54:
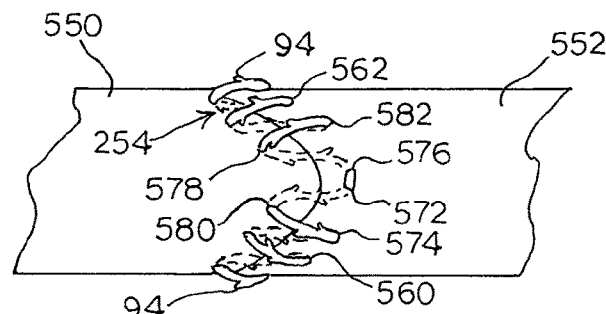
Figure 55:
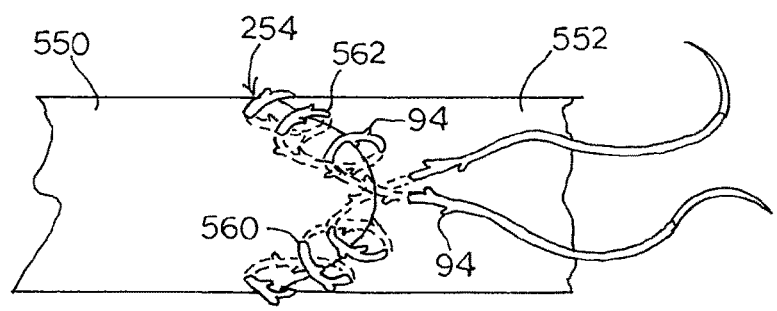

FIG. 54 shows another method of using a bi-directional barbed suture 254 for joining the ends 550, 552 of a bodily tube. Beginning at an initial insertion point 572, an end of a first portion 560 of the suture 254 is inserted through the wall of a first end 552 of the tube. The end of the first portion 560 of the suture 254 is then inserted from the interior of the tube through the wall of a second end 550 of the tube. The first portion 560 of the suture 254 may be pulled through the walls of the tube until the opposed barbs on a second portion 562 of the suture 254 contact the outer surface of the wall of the first end 552 of the tube for drawing the two ends 550, 552 of the tube together. The end of the first portion 560 of the suture 254 is inserted through the wall and into the interior of the first end 552 of the tube at a point 574 circumferentially spaced in a first direction from the initial insertion point 572. The end of the second portion 562 of the suture 254 is inserted through the wall of the first end 552 of the tube at a point 576 adjacent the initial insertion point 572 of the first portion 560 of the suture 254, which practically functions as the same point of insertion. The end of the second portion 562 of the suture 254 is then inserted from the interior of the tube through the wall of the second end 550 of the tube at a point 578 circumferentially spaced from the first exit point 580 of the end of the first portion 560 of the suture 254. The end of the second portion 562 of the suture 254 is then inserted through the wall of the first end 552 of the tube at a point 582 circumferentially spaced in a second direction from the initial insertion point 576. These steps are repeated for advancing each end of the barbed suture 254 around the tube. After the last bite, the suture pattern may be completed with a terminal J-stitch or S-stitch at each end. Alternatively, the suture pattern may continue as described until the ends of the suture cross one another, as shown in FIG. 55. Even then the suture pattern may be completed with a terminal J-stitch or S-stitch, if desired.

In the method for joining the ends of a tube according to the present invention, the path of insertion of the end of the suture through the tube may include a longitudinal component as the suture is advanced through the tissue of the tube. Using this technique, more of the length of the suture is placed in the tissue of the tube, which may result in better holding strength. Additionally, effective joining of the ends of a tube within the body can be achieved using the methods described herein regardless of where the barbed suture initially enters the tube along the periphery of the free end.

It is understood that although the methods of joining two ends of a bodily tube is shown and described, the present invention is not so limited. In particular, the methods according to the present invention may include a procedure wherein a portion of tube is grafted between the ends of the original tube. This is a procedure particularly used in coronary artery bypass grafting, or CABG. The grafting procedure is similar to the methods described herein except that the ends of the graft are attached to the ends of the tube using the suture methods described above.

The invention is further illustrated by the following non-limiting example.

EXAMPLE

Figure 56:
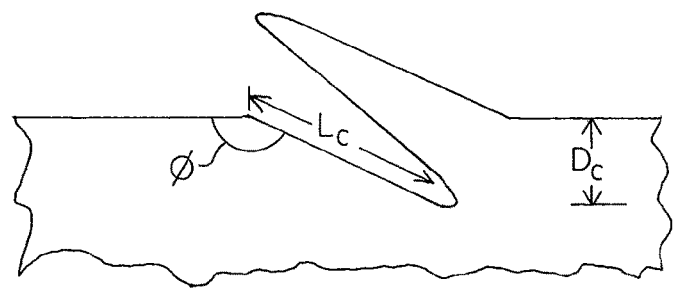
FIG. 56 is a detail view of an embodiment according to the present invention of a barb configuration.

Testing was performed comparing the tissue holding capacity of a bi-directional barbed suture placed in tissue with a J-stitch at each end with a conventional knotted suture. Two different barb geometry designs (A and B) of a bi-directional barbed suture were fabricated from polydioxanone (PDO), size 0. Each suture was 7 inches long and included 78 barbs, equally divided into two opposing segments, in the middle 3 inches. The spirality of Design A was 12.8 degrees, and the spirality of Design B was 12.4 degrees. The average straight-pull tensile strength of each design was measured using ten samples. Using an Optem Zoom microscope (made by Thales Optem Inc. of Fairport, N.Y.) with an attached video camera, the barb geometries were characterized by four different parameters: cut angle ($\phi$); cut depth ($D_c$); calculated cut length ($L_c$); and the distance between cuts (FIG. 56).

The straight-pull tensile strengths and barbed geometries of the barb sutures were determined to be as shown in Table 1.

TABLE 1

| Parameters | Design A | Design B |
| --- | --- | --- |
| Tensile strength (lb.) | 7.12 ± 0.25 | 9.89 ± 0.34 |
| Cut angle, $\phi$(°) | 152.3 ± 0.8 | 162.2 ± 2.2 |
| Cut depth, $D_c$ (mm) | 0.25 ± 0.01 | 0.12 ± 0.02 |
| Cut length, $L_c$ (mm) | 0.54 ± 0.02 | 0.38 ± 0.04 |
| Distance between cuts (mm) | 0.82 ± 0.01 | 0.91 ± 0.04 |

Figure 57:
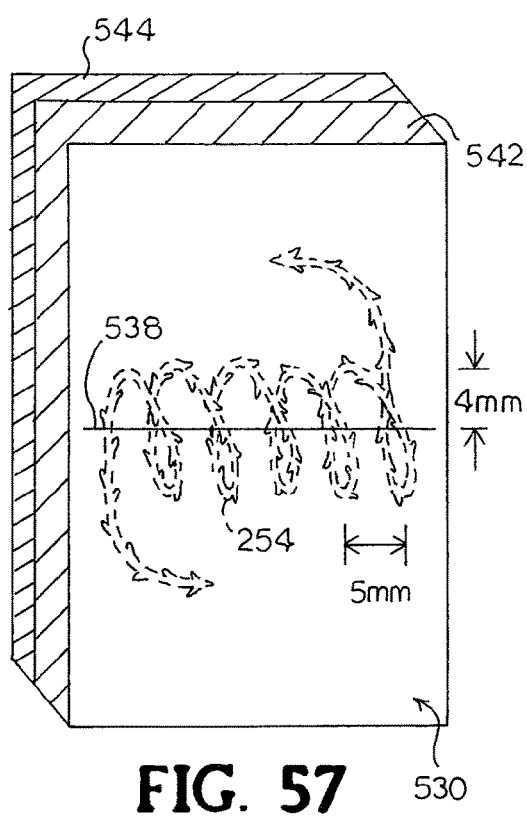
FIG. 57 is a plan view of an example performed according to the present invention for joining two sides of an open wound in tissue.
Figure 58:
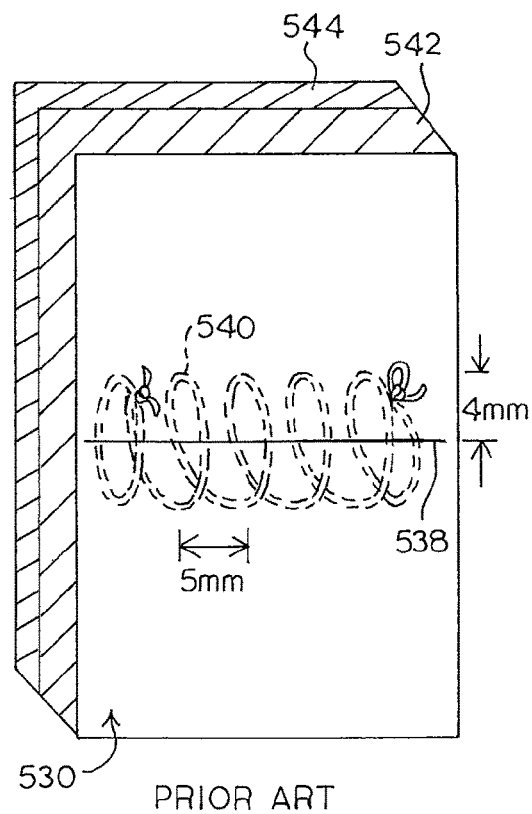
FIG. 58 is a plan view of an example performed according to a conventional method for joining two sides of an open wound in tissue.

Referring to FIGS. 57 and 58, a full-thickness, 3-cm incision was created in the distal jejunum 530 of a cadaveric pig perpendicular to its length. The jejunal segment measured about 10 cm in outer circumference and 5 mm in thickness. Each wound 538 was excised so that it was centered on a 4 cm by 15 cm piece of tissue. The wound 538 was closed with either a barbed suture 254 including the two Designs A and B as shown in FIG. 57, or control PDS II (polydioxanone) suture 540 as shown in FIG. 58, all of size 0, using a running "over-and-over" technique. Suture strands, in the serosa 542 and mucosa 544, engaged but did not perforate the mucosal layer. A knot (5 throws) anchored each end of the control suture, whereas the barbed suture 254 was finished with and without a J-stitch bite through adjacent tissue. Bite size (4 mm), distance between bites (5 mm), and number of crosses of the incision (11) were equivalent in all suture types. Wound edges were cut such that only the sutures held the two halves together. Ten sutured tissue specimens of each suture type were tested on a Test Resources Universal Tester, model 200Q (made by DDL of Eden Prairie, Minn.), with a 250 lb. load cell, a 5 cm gauge length, and a crosshead speed of 5 cm/sec. Each specimen was stretched to failure, wherein the sutures tore through the tissue to the wound and the two pieces of tissue separated, and the maximum load was recorded.

The average peak forces required to separate the pig intestinal wounds are shown in Table 2:

TABLE 2

| Sutures, size 0 | Tissue Holding Capacity (lb.) |
| --- | --- |
| Barbed PDO, A with terminal J-Stitch | 7.64 ± 1.39 |
| Barbed PDO, A without terminal J-Stitch | 4.53 ± 1.07 |
| Barbed PDO, B with terminal J-Stitch | 8.40 ± 1.83 |
| Control PDS II | 6.61 ± 2.02 |

By comparison with the U.S. Pharmacopoeia minimum knot-pull tensile strength requirement of size 0 absorbable sutures, 8.60 lb., the tensile strength of barbed PDO Design A, appears inferior. However, the Design A wound holding capacity using a terminal J-stitch compares favorably to that of the same-size control in the pig intestinal model (p=0.19). Further, Design B with a terminal J-stitch not only exceeds the U.S. Pharmacopoeia requirement, but also demonstrates a trend toward higher mechanical performance than the conventional suture. The wound holding strength omitting the J-stitches and using Design A was inferior to the holding capacity of Design A with J-stitches. Some of this reduction may be the result of the shorter length of suture in the tissue with J-stitches omitted, but it is believed that most of the difference is the result of omitting the J-stitch configuration.

Although the present invention has been shown and described in considerable detail with respect to only a few exemplary embodiments thereof, it should be understood by those skilled in the art that we do not intend to limit the invention to the embodiments shown and described since various modifications, omissions and additions may be made to the disclosed embodiments without materially departing from the novel teachings and advantages of the invention, particularly in light of the foregoing teachings. For example, the barbed sutures with one or more J-stitches and S-stitches and the single-directional sutures with anchors may be used in a wide variety of applications, including but not limited to Nissen fundoplications, stabilization of bowel structures during laparoscopic surgery, appendectomy, Zenker's Diverticulum surgery, urinary bladder cystostomy, securing a replacement heart valve, securing external devices to tissue, and closing axial wounds in blood vessels. Accordingly, we intend to cover all such modifications, omission, additions and equivalents as may be included within the spirit and scope of the invention.

What is claimed is:

1. A barbed suture comprising:
   (a) an elongated body with a cross section, where the cross section has a transverse length;
   (b) one pointed end, wherein the pointed end includes a needle;
   (c) a proximal end; and
   (d) a plurality of staggered cuts in the elongated body providing for a plurality of staggered barbs extending from the periphery of the elongated body, the barbs yielding toward the elongated body during movement of the barbed suture through tissue in the direction of movement of the pointed end and the barbs resisting movement of the barbed suture through the tissue in a direction opposite the direction of movement of the pointed end by engagement of the barbs within the tissue;

the proximal end having a loop through which the elongated body may pass to secure tissue as an anchor, wherein the anchor does not include barbs on the loop, the anchor preventing movement of the barbed suture in the direction of movement of the pointed end, wherein the barbs are characterized by a barb cut depth (Dc), wherein the ratio of the barb cut depth to the transverse length is about 0.05 to about 0.6, wherein the barbs are characterized by a barb cut angle (Ø), wherein the barb cut angle ranges from 140 to 175 degrees, wherein the barbs are characterized by a barb cut length (Lc), wherein the ratio of the barb cut length to transverse length is about 0.2 to about 2, wherein the barbs are characterized by a longitudinal distance between barbs cut into the elongated body, wherein the ratio of the longitudinal distance between barbs to the transverse length is about 0.1 to 6, wherein the barbs are arranged in a helical pattern such that two or more barbs are not laterally adjacent one another along the periphery of the elongated body.

2. The barbed suture of claim 1, wherein the loop has an inner perimeter and an outer perimeter, wherein the inner perimeter of the loop is uninterrupted by any surface features that are configured to affect the pointed end passing through the inner perimeter of the loop.

3. The barbed suture of claim 1, wherein the loop has an inner perimeter and an outer perimeter, wherein the inner perimeter has a curved proximal end and a pointed distal end, with continuously curved lateral edges extending from the curved proximal end to the pointed distal end.

4. The barbed suture of claim 1, wherein the needle is integral with the elongated body.

5. The barbed suture of claim 1, wherein the number of barbs in the helical pattern that occupy one revolution is not an integer.

6. The barbed suture of claim 1, wherein the barbs are arranged in three rows along the elongated body, wherein the rows are spaced 120 degrees from one another around the circumference of the elongated body.

7. The barbed suture of claim 1, wherein the transverse length is about 100 to 500 microns.

8. The barbed suture of claim 1, wherein the loop has a diameter such that the barbed suture can pass through the loop without the barbs on the elongated body engaging the loop.

9. A barbed suture comprising:
(a) a pointed end including a needle;
(b) an elongated body, the needle being secured to the elongated body, the elongated body having a periphery and a generally circular cross-section with a diameter, wherein a plurality of staggered cuts in the elongated body provide a plurality of staggered barbs extending from the periphery, an entirety of a barb adapted to yield toward the elongated body during movement of the barbed suture through tissue in a direction of movement of the pointed end and resist movement of the barbed suture through the tissue in a direction opposite the direction of movement of the pointed end by engagement of the barbs within the tissue; and
(c) one end opposite the pointed end having a loop through which the elongated body may pass to secure tissue as an anchor wherein the anchor does not include barbs on the loop, the anchor preventing movement of the barbed suture in the direction of movement of the pointed end, wherein the barbs are characterized by a barb cut depth (Dc), wherein the ratio of the barb cut depth to the transverse length is about 0.05 to about 0.6, wherein the barbs are characterized by a barb cut angle (Ø), wherein the barb cut angle ranges from 140 to 175 degrees, wherein the barbs are characterized by a barb cut length (Lc), wherein the ratio of the barb cut length to transverse length is about 0.2 to about 2, wherein the barbs are characterized by a longitudinal distance between barbs cut into the elongated body, wherein the ratio of the longitudinal distance between barbs to the transverse length is about .1 to 6, wherein the barbs are arranged in a helical pattern such that two or more barbs are not laterally adjacent one another along the periphery of the elongated body.

10. The barbed suture of claim 9, wherein the loop has an inner perimeter and an outer perimeter, wherein the inner perimeter of the loop is uninterrupted by any surface features that are configured to affect the pointed end passing through the inner perimeter of the loop.

11. The barbed suture of claim 9, wherein the loop has an inner perimeter and an outer perimeter, wherein the inner perimeter has a curved proximal end and a pointed distal end, with continuously curved lateral edges extending from the curved proximal end to the pointed distal end.

12. The barbed suture of claim 9, wherein the needle is integrally secured to the elongated body.

13. The barbed suture of claim 9, wherein the number of barbs in the helical pattern that occupy one revolution is not an integer.

14. The barbed suture of claim 9, wherein the barbs are arranged in three rows along the elongated body, where the rows are spaced 120 degrees from one another around circumference of the elongated body.

15. A barbed suture comprising:
(a) a needle;
(b) an elongated body, the needle being attached to the elongated body, the elongated body being generally circular in cross-section and having a periphery, the elongated body being flexible and substantially nonresilient, the elongated body having a plurality of staggered cuts that give rise to a plurality of barbs staggered along the periphery of the elongated body and being adapted to yield toward the elongated body during movement of the barbed suture through tissue in a direction of movement of the needle and resist movement of the barbed suture through the tissue in a direction opposite the direction of movement of the needle by engagement of the barbs with tissue surrounding the elongated body; and
(c) one end opposite the needle having a loop through which the needle and elongated body may pass to secure tissue as an anchor wherein the anchor does not include barbs on the loop, the anchor preventing movement of the elongated body in the direction of movement of the needle, wherein the barbs are characterized by a barb cut depth (Dc), wherein the ratio of the barb cut depth to the transverse length is about 0.05 to about 0.6, wherein the barbs are characterized by a barb cut angle (Ø), wherein the barb cut angle ranges from 140 to 175 degrees, wherein the barbs are characterized by a barb cut length (Lc), wherein the ratio of the barb cut length to transverse length is about 0.2 to about 2, wherein the barbs are characterized by a longitudinal distance between barbs cut into the elongated body, wherein the ratio of the longitudinal distance between barbs to the transverse length is about 0.1 to 6, wherein the barbs are arranged in a helical pattern such that two or more barbs are not laterally adjacent one another along the periphery of the elongated body.

16. The barbed suture of claim 15, wherein the loop has an inner perimeter and an outer perimeter, wherein the inner perimeter of the loop is uninterrupted by any surface features that are configured to affect the needle passing through the inner perimeter of the loop.

17. The barbed suture of claim 15, wherein the loop has an inner perimeter and an outer perimeter, wherein the inner perimeter has a curved proximal end and a pointed distal end, with continuously curved lateral edges extending from the curved proximal end to the pointed distal end.

18. The barbed suture of claim 15, wherein the number of barbs in the helical pattern that occupy one revolution is not an integer.

19. The barbed suture of claim 15, wherein the barbs are arranged in three rows along the elongated body, where the rows are spaced 120 degrees from one another around the circumference of the elongated body.

20. A barbed suture comprising:
   (a) an elongated body with a cross section, where the cross section has a transverse length;
   (b) one pointed end;
   (c) a proximal end; and
   (d) a plurality of staggered cuts in the elongated body providing for a plurality of staggered barbs extending from a periphery of the elongated body, the barbs yielding toward the elongated body during movement of the barbed suture through tissue in the direction of movement of the pointed end and the barbs resisting movement of the barbed suture through the tissue in a direction opposite the direction of movement of the pointed end by engagement of the barbs within the tissue;
   the proximal end having a loop through which the elongated body may pass to secure one end but not both ends of the barbed suture to tissue as an anchor wherein the anchor does not include barbs on the loop, the anchor preventing movement of the barbed suture in the direction of movement of the pointed end,
   wherein the barbs are characterized by a barb cut depth (Dc), wherein the ratio of the barb cut depth to the transverse length is about 0.05 to about 0.6,
   wherein the barbs are characterized by a barb cut angle (Ø), wherein the barb cut angle ranges from 140 to 175 degrees,
   wherein the barbs are characterized by a barb cut length (Lc), wherein the ratio of the barb cut length to transverse length is about 0.2 to about 2,
   wherein the barbs are characterized by a longitudinal distance between barbs cut into the elongated body, wherein the ratio of the longitudinal distance between barbs to the transverse length is about 0.1 to 6,
   wherein the barbs are arranged in a helical pattern such that two or more barbs are not laterally adjacent one another in the cross-section.

21. The barbed suture of claim 20, wherein the loop has an inner perimeter and an outer perimeter, wherein the inner perimeter of the loop is uninterrupted by any surface features that are configured to affect the pointed end passing through the inner perimeter of the loop.

22. The barbed suture of claim 20, wherein the loop has an inner perimeter and an outer perimeter, wherein the inner perimeter has a curved proximal end and a pointed distal end, with continuously curved lateral edges extending from the curved proximal end to the pointed distal end.

23. The barbed suture of claim 20, wherein the number of barbs in the helical pattern that occupy one revolution is not an integer.

24. The barbed suture of claim 20, wherein the barbs are arranged in three rows along the elongated body, where the rows are spaced 120 degrees from one another around the circumference of the elongated body.

25. A barbed suture comprising:
   (a) a pointed end including a needle;
   (b) an elongated body, the needle being secured to the elongated body, the elongated body having a periphery and a generally circular cross-section with a diameter, wherein a plurality of staggered cuts in the elongated body provide a plurality of staggered barbs extending from the periphery, an entirety of a barb adapted to yield toward the elongated body during movement of the barbed suture through the tissue in a direction of movement of the pointed end and resist movement of the barbed suture through tissue in a direction opposite the direction of movement of the pointed end by engagement of the barbs within the tissue; and
   (c) one end opposite the pointed end having a loop through which the elongated body may pass to secure tissue as an anchor wherein the anchor does not include barbs on the loop, the anchor preventing movement of the barbed suture in the direction of movement of the pointed end,
   wherein the barbs are characterized by a barb cut depth (Dc), wherein the ratio of the barb cut depth to the transverse length is about 0.05 to about 0.6,
   wherein the barbs are characterized by a barb cut angle (Ø), wherein the barb cut angle ranges from 140 to 175 degrees,
   wherein the barbs are characterized by a barb cut length (Lc), wherein the ratio of the barb cut length to transverse length is about 0.2 to about 2,
   wherein the barbs are characterized by a longitudinal distance between barbs cut into the elongated body, wherein the ratio of the longitudinal distance between barbs to the transverse length is about 0.1 to 6,
   wherein the barbs are arranged in a helical pattern,
   wherein the loop has an inner perimeter and an outer perimeter, wherein the inner perimeter of the loop is uninterrupted by any surface features that are configured to affect the pointed end passing through the inner perimeter of the loop.

26. A barbed suture comprising:
   (a) a pointed end including a needle;
   (b) an elongated body, the needle being secured to the elongated body, the elongated body having a periphery and a generally circular cross-section with a diameter, wherein a plurality of staggered cuts in the elongated body provide a plurality of staggered barbs extending from the periphery, an entirety of a barb adapted to yield toward the elongated body during movement of the barbed suture through tissue in a direction of movement of the pointed end and resist movement of the barbed suture through the tissue in a direction opposite the direction of movement of the pointed end by engagement of the barbs within the tissue; and (c) one end opposite the pointed end having a loop through which the elongated body may pass to secure tissue as an anchor wherein the anchor does not include barbs on the loop, the anchor preventing movement of the barbed suture in the direction of movement of the pointed end, wherein the barbs are characterized by a barb cut depth (Dc), wherein the ratio of the barb cut depth to the transverse length is about 0.05 to about 0.6, wherein the barbs are characterized by a barb cut angle (Ø), wherein the barb cut angle ranges from 140 to 175 degrees, wherein the barbs are characterized by a barb cut length (Lc), wherein the ratio of the barb cut length to transverse length is about 0.2 to about 2, wherein the barbs are characterized by a longitudinal distance between barbs cut into the elongated body, wherein the ratio of the longitudinal distance between barbs to the transverse length is about 0.1 to 6, wherein the barbs are arranged in a helical pattern, wherein the loop has an inner perimeter and an outer perimeter, wherein the inner perimeter has a curved proximal end and a pointed distal end, with continuously curved lateral edges extending from the curved proximal end to the pointed distal end.

27. A barbed suture comprising:
(a) an elongated body with a cross section, where the cross section has a transverse length;
(b) one pointed end;
(c) a proximal end; and
(d) a plurality of staggered cuts in the elongated body providing for a plurality of staggered barbs extending from a periphery of the elongated body, the barbs yielding toward the elongated body during movement of the barbed suture through the tissue in the direction of movement of the pointed end and the barbs resisting movement of the barbed suture through tissue in a direction opposite the direction of movement of the pointed end by engagement of the barbs within the tissue;

the proximal end having a loop through which the elongated body may pass to secure one end but not both ends of the barbed suture to tissue as an anchor wherein the anchor does not include barbs on the loop, the anchor preventing movement of the barbed suture in the direction of movement of the pointed end, wherein the barbs are characterized by a barb cut depth (Dc), wherein the ratio of the barb cut depth to the transverse length is about 0.05 to about 0.6, wherein the barbs are characterized by a barb cut angle (Ø), wherein the barb cut angle ranges from 140 to 175 degrees, wherein the barbs are characterized by a barb cut length (Lc), wherein the ratio of the barb cut length to transverse length is about 0.2 to about 2, wherein the barbs are characterized by a longitudinal distance between barbs cut into the elongated body, wherein the ratio of the longitudinal distance between barbs to the transverse length is about 0.1 to 6, wherein the barbs are arranged in a helical pattern, wherein the loop has an inner perimeter and an outer perimeter, wherein the inner perimeter of the loop is uninterrupted by any surface features that are configured to affect the pointed end passing through the inner perimeter of the loop.

28. A barbed suture comprising:
(a) an elongated body with a cross section, where the cross section has a transverse length;
(b) one pointed end;
(c) a proximal end; and
(d) a plurality of staggered cuts in the elongated body providing for a plurality of staggered barbs extending from a periphery of the elongated body, the barbs yielding toward the elongated body during movement of the barbed suture through tissue in the direction of movement of the pointed end and the barbs resisting movement of the barbed suture through the tissue in a direction opposite the direction of movement of the pointed end by engagement of the barbs within the tissue;

the proximal end having a loop through which the elongated body may pass to secure one end but not both ends of the barbed suture to tissue as an anchor wherein the anchor does not include barbs on the loop, the anchor preventing movement of the barbed suture in the direction of movement of the pointed end, wherein the barbs are characterized by a barb cut depth (Dc), wherein the ratio of the barb cut depth to the transverse length is about 0.05 to about 0.6, wherein the barbs are characterized by a barb cut angle (Ø), wherein the barb cut angle ranges from 140 to 175 degrees, wherein the barbs are characterized by a barb cut length (Lc), wherein the ratio of the barb cut length to transverse length is about 0.2 to about 2, wherein the barbs are characterized by a longitudinal distance between barbs cut into the elongated body, wherein the ratio of the longitudinal distance between barbs to the transverse length is about 0.1 to 6, wherein the barbs are arranged in a helical pattern, wherein the loop has an inner perimeter and an outer perimeter, wherein the inner perimeter has a curved proximal end and a pointed distal end, with continuously curved lateral edges extending from the curved proximal end to the pointed distal end.

* * * * *